US007211117B2

(12) United States Patent
Guerin et al.

(10) Patent No.: US 7,211,117 B2
(45) Date of Patent: May 1, 2007

(54) COMPOSITION FOR DYEING KERATIN FIBERS COMPRISING AT LEAST ONE DYE CHOSEN FROM MONOHETEROYLDIARYLMETHANE DIRECT DYES AND THE LEUCO PRECURSORS THEREOF AND DYEING METHOD USING IT

(75) Inventors: Frédéric Guerin, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 58 days.

(21) Appl. No.: 10/745,634

(22) Filed: Dec. 29, 2003

(65) Prior Publication Data

US 2004/0216247 A1 Nov. 4, 2004

Related U.S. Application Data

(60) Provisional application No. 60/450,332, filed on Feb. 28, 2003.

(30) Foreign Application Priority Data

Dec. 30, 2002 (FR) .................................. 02 16851

(51) Int. Cl.
   *A61K 7/13* (2006.01)
(52) U.S. Cl. ..................... 8/405; 8/406; 8/407; 8/426; 8/568; 8/570; 8/573; 8/659; 546/165
(58) Field of Classification Search .................. 8/405, 8/406, 407, 426, 568, 570, 573, 659; 546/165
   See application file for complete search history.

(56) References Cited

U.S. PATENT DOCUMENTS

| | | | |
|---|---|---|---|
| 3,418,117 A | 12/1968 | Becker ............................. 96/3 |
| 3,423,427 A | 1/1969 | Cescon et al. ............... 260/329 |
| 3,627,893 A | 12/1971 | Seeger ........................ 424/258 |
| 3,652,556 A | 3/1972 | Kühlthau et al. ............... 8/177 |
| 3,685,956 A | 8/1972 | Raue et al. .................. 260/242 |
| 3,995,088 A | 11/1976 | Garner et al. ............... 428/323 |
| 4,054,718 A | 10/1977 | Garner et al. ............... 428/454 |
| 4,154,463 A | 5/1979 | Burri |
| 4,254,032 A | 3/1981 | Petitpierre et al. |
| 4,340,540 A | 7/1982 | Hermann .................... 548/440 |
| 4,355,823 A | 10/1982 | Burri |
| 4,407,960 A | 10/1983 | Tratnyek ........................ 436/1 |
| 4,598,036 A | 7/1986 | Iwasaki et al. |
| 4,823,985 A | 4/1989 | Grollier et al. ................. 222/1 |
| 5,094,688 A * | 3/1992 | Eckstein et al. ........... 106/31.2 |
| 5,097,034 A * | 3/1992 | Eckstein ..................... 546/165 |
| 5,266,699 A | 11/1993 | Naef et al. |
| 5,362,612 A | 11/1994 | Kiekens et al. |
| 5,708,151 A | 1/1998 | Möckli ........................ 534/608 |
| 5,733,343 A | 3/1998 | Mockli |
| 5,888,252 A | 3/1999 | Mockli |

| | | |
|---|---|---|
| 2003/0066143 A1 | 4/2003 | Mockli |

FOREIGN PATENT DOCUMENTS

| | | |
|---|---|---|
| BE | 702 240 | 2/1968 |
| DE | 1 248 193 | 10/1964 |
| DE | 1 254 118 | 5/1968 |
| DE | 1254118 * | 5/1968 |
| DE | 1 620 564 | 5/1970 |
| DE | 1 569 749 | 1/1971 |
| DE | 1 569 750 | 1/1971 |
| DE | 156750 * | 1/1971 |
| DE | 29 17 271 | 11/1980 |
| DE | 2917271 * | 11/1980 |
| EP | 822846 * | 11/1959 |
| EP | 0 714 954 | 6/1996 |
| FR | 2 188 202 | 1/1974 |
| FR | 2 586 913 | 3/1987 |
| GB | 822 846 | 11/1959 |
| GB | 876 663 | 9/1961 |
| GB | 1 047 796 | 11/1966 |
| GB | 1 139 407 | 1/1969 |
| GB | 1 188 605 | 4/1970 |
| GB | 2 075 539 | 11/1981 |
| GB | 2 180 215 | 3/1987 |
| JP | 59-162553 | 9/1984 |
| JP | 62201967 * | 9/1987 |
| JP | 08179465 A * | 7/1996 |
| WO | WO 95/01772 | 1/1995 |
| WO | WO 95/15144 | 6/1995 |
| WO | WO 01/66646 | 9/2001 |

OTHER PUBLICATIONS

English Abstract of the Japanese Patent No. JP 62201967.*
English Abstract of the Japanese Patent No. JP 09179465 A.*
STIC Search Report.*
English language Derwent Abstract of DE 1 254 118, May 22, 1968.
English language Derwent Abstract of DE 1 569 749, Jan. 21, 1971.
English language Derwent Abstract of DE 1 569 750, Jan. 21, 1971.
English language Derwent Abstract of DE 1 620 564, May 14, 1970.
English language Derwent Abstract of DE 29 17 271, Nov. 6, 1980.
Barker et al., "Steric Effects in Di- and Tri-arylmethanes. Part 1X. Electronic Absorption Spectra of Julolidine (2,3,6,7-Tetrahydro-1H, 5H-benzo[ij]quinolizine) and Kairoline (1-Methyl-1,2,3,4,-tetrahydroquinoline) Analogues of Michler's Hydrol Blue, Malachite Green, Crystal Violet, and Michler's Ketone," J. Chem. Soc. (B), pp. 1068-1071, 1969.

(Continued)

*Primary Examiner*—Eisa Elhilo
(74) *Attorney, Agent, or Firm*—Finnegan Henderson Farabow Garrett & Dunner LLP

(57) ABSTRACT

A composition for dyeing keratin fibers, for example, human keratin fibers, such as hair, comprising at least one dye chosen from heteroyldiarylmethane type direct dyes, for example, monoheteroyidiarylmethane direct dyes, and the leuco precursors thereof; and also to methods for dyeing keratin fibers, for example, human keratin fibers, such as hair, using the composition, and multi-compartment devices.

39 Claims, No Drawings

OTHER PUBLICATIONS

Copending U.S. Appl. No. 10/746,497, filed Dec. 29, 2003.
Copending U.S. Appl. No. 10/746,501, filed Dec. 29, 2003.
English language Derwent Abstract of FR 2 188 202, Jan. 18, 1974.
English language Derwent Abstract of JP 59-162553, Sep. 13, 1984.
French Search Report of French Patent Application No. 0216845, dated Nov. 21, 2003.
French Search Report of French Patent Application No. 0216849, dated Sep. 3, 2003.
French Search Report of French Patent Application No. 0216851, dated Oct. 8, 2003.
Office Action in co-pending U.S. Appl. No. 10/746,497, dated Oct. 20, 2005.
Office Action in co-pending U.S. Appl. No. 10/746,501, dated Oct. 20, 2005.
Shikhakiev: Izvestiya Vysshikh Uchebnykh Zavedenii, Khimiya I Khimicheskaya Tekhnologiya, vol. 42, No. 4, 1999, pp. 83-87, Abstract.

* cited by examiner

COMPOSITION FOR DYEING KERATIN FIBERS COMPRISING AT LEAST ONE DYE CHOSEN FROM MONOHETEROYLDIARYLMETHANE DIRECT DYES AND THE LEUCO PRECURSORS THEREOF AND DYEING METHOD USING IT

This application claims benefit of U.S. Provisional Application No. 60/450,332, filed Feb. 28, 2003.

Disclosed herein are compositions for dyeing (tinting) keratin fibers, for example, human keratin fibers, such as hair, comprising at least one dye chosen from heteroyldiarylmethane direct dyes, for example, monoheteroyidiarylmethane direct dyes and the leuco precursors thereof.

Further disclosed herein are methods for dyeing keratin fibers, for example, human keratin fibers, such as hair using the composition.

There are many compositions and many methods of dyeing keratin fibers, such as human hair. It is known that keratin fibers, such as human hair, can be dyed with dye compositions comprising oxidation dye precursors, such as ortho and paraphenylenediamines, ortho and para-aminophenols, heterocyclic compounds such as derivatives of diaminopyrazole, usually called "oxidation bases". Oxidation dye precursors, and oxidation bases, are colorless or slightly colored compounds, that, when combined with oxidizing products, may produce colored and coloring compounds by an oxidizing condensation process.

It is also known that the shades obtained with these oxidation bases can be varied by combining them with "couplers" or color modifiers, that may be chosen, for example, from aromatic metadiamines, meta-aminophenols, metadiphenols and some heterocyclic compounds. The variety of molecules used as oxidation bases and couplers may make it possible to obtain a wide range of color.

"Permanent" coloring obtained using oxidation dyes can also, moreover, satisfy at least one of a certain number of desirable characteristics, such as no toxicological disadvantages; possibility of obtaining shades of the required intensity; and resistant to external agents, such as light, bad weather, washing, permanent waving, sweat and friction.

Desirably, the dyes can also cover white hair, and finally can be the least selective as possible, making it possible to obtain the smallest possible coloration differences along the length of a keratin fiber, which can be sensitised differently, in other words the fiber can be damaged between its end and its root.

Thus, it can be seen that although conventional base-coupler combinations may be used to obtain a wide range of colors, they may not satisfy at least one of the desirable characteristics listed above and, for example, may often lead to the production of varied and badly defined coupling products being created in the fiber, that may cause innocuousness and/or toughness that may be difficult to control, for example such as selective color changing.

Another method of dyeing keratin fibers, such as hair, is to use direct dyes.

The direct dyes that are conventionally used can be chosen from nitrated benzenic, anthraquinonic, nitropyridinic, azoic, cationic azoic, xanthenic, azinic acridinic, triarylmethanic, nitrated benzenic type, and natural dyes.

These direct dyes, comprising colored and coloring molecules with an affinity for fibers, may be applied to keratin fibers for a sufficiently long time to obtain the required color, and may then be rinsed.

Consequently, direct dyes are now widely used since they also have some advantages compared with oxidation dyes precursors and, for example, may reduce potential allergy risks and also the lack of sensitisation of the hair due to the oxidation process.

However, the colorations obtained can be temporary or semi-permanent, since the nature of the interactions that bind the direct dyes to the keratin fibers, and their desorption from the surface and/or the core of the fiber can be responsible for low dyeing capacity and poor resistance to washing, bad weather or sweat. These direct dyes may also be sensitive to light since the resistance of chromophore to photochemical attack is low, which may cause fading of the hair color over time.

Therefore, there is a need for a dye composition for dyeing keratin fibers, for example, human keratin fibers, such as hair, that can have at least one of the following advantages: fully innocuous, fully compatible with keratin fibers, that is only very slightly selective, that produces a large variety of bright colors and that is also capable of creating a tough, stable keratin fiber coloration resistant to external agents such as light, bad weather, washing, sweat, friction and subsequent treatments such as permanent wavings.

There is also a need for a dye composition for the treatment of all sorts of keratin fibers of all hair types, for example white hair, even if this hair has already been treated, for example, with a discoloration or permanent waving treatment.

Finally, there is a need for a composition that dyes without it being necessary to first sensitize the keratin fibers of the hair.

One aim of the present inventors was to provide a keratin fiber dye composition, for example, for human keratin fibers, such as hair, that meets, among others, at least one of the needs mentioned above.

Another aim is to supply a keratin fiber dye composition that does not have at least one of the disadvantages, defects, limitations and drawbacks of dye compositions of the prior art, e.g. dye compositions involving a base-coupler combination, or compositions using a direct dye.

At least one of these aims may be achieved with the compositions disclosed herein for dyeing keratin fibers, comprising, in a medium suitable for dyeing, at least one dye chosen from formulae (I), (Ibis), (II) and (IIbis) and the tautomeric forms thereof and the addition salts thereof

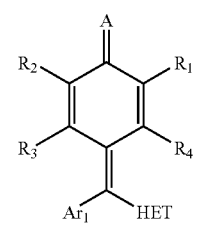

(I)

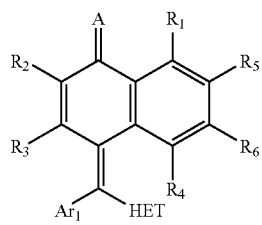

(Ibis)

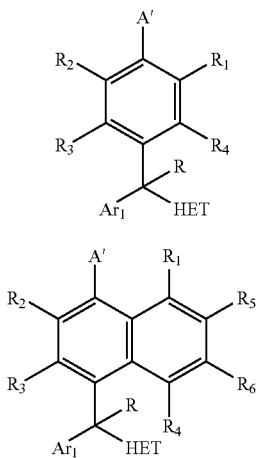

wherein:
Ar₁, which may be identical or different, is chosen from aryl, such as phenyl and naphthyl, optionally substituted with at least one Z group;
HET, which may be identical or different, is chosen from heterocycles optionally substituted with at least one Z' group;
A, which may be identical or different, is chosen from O; NH; N-alkyl; N-hydroxyalkyl; ammonium, N-alkylammonium, N-(hydroxyalkyl)ammonium, N,N-dialkylammonium, N,N-di(hydroxyalkyl)ammonium, and N-(hydroxyalkyl)N-(alkyl)ammonium, wherein the two alkyl groups may form, together with the nitrogen atom to which they are bonded, at least one cyclic group optionally interrupted by at least one atom chosen from nitrogen, oxygen and sulphur;
$R_1$ to $R_6$, Z, and Z', which may be identical or different, are each chosen from hydrogen, halogens, such as F, Cl, Br and I, —NHSO₃H; hydroxyl; alkyl; alkoxy; alkylthio; monoalkylamino; and dialkylamino, wherein the two alkyl groups of the dialkylamino may form together with the nitrogen atom to which they are bonded, at least one cyclic group optionally interrupted by at least one atom chosen from nitrogen, oxygen and sulphur; heterocycle and nitro; aryl; acyl; alkoxycarbonyl; carboxamido; cyano; —CO₂H; —SO₃H; —PO₃H₂; and —PO₄H₂;
A', which may be identical or different, is chosen from hydrogen; hydroxyl; amino; (hydroxyalkyl)amino; monoalkylamino; di(hydroxyalkyl)amino, (hydroxyalkyl) (alkyl)amino, and (dialkyl)amino, wherein the two alkyl groups of the (dialkyl)amino may form together, with the nitrogen atom to which they are bonded, at least one cyclic group optionally interrupted by at least one atom chosen from nitrogen, oxygen and sulphur; and
R is chosen from hydrogen, halogen, hydroxyl, alkoxy, and alkylthio.

In one embodiment, HET is chosen from unsaturated heterocycles, for example, an aromatic heterocycle, optionally substituted with at least one Z' group.

In formulae (I), (Ibis) and (II), (IIbis) above, the term "alkyl" used for alkyl radicals and for groups comprising an alkyl part, means a straight or branched carbon chain comprising, for example, from 1 to 30, further, for example, from 1 to 8 and even further, for example, from 1 to 4 carbon atoms, that may be carried and/or interrupted with at least one atom chosen from oxygen, sulphur and nitrogen, and that may be substituted with at least one substituent chosen from halogens such as chlorine, bromine, iodine and fluorine; heterocycles; aryl; hydroxyl; alkoxy; amino; acyl; carboxamido; —CO₂H; SO₃H; —PO₃H₂; —PO₄H₂; —NHSO₃H; sulphonamide; monoalkylamino; trialkylammonium radicals; and dialkylamino radicals wherein the two alkyl groups can form, together with the nitrogen atom of the dialkylamino to which they are bonded, at least one cyclic group optionally interrupted by at least one atom chosen from nitrogen, oxygen and sulphur.

Similarly and unless mentioned otherwise, as used herein the term "alkoxy" used for alkoxy radicals and for groups comprising an alkoxy part means an O-alkyl chain, the term alkyl having the meaning mentioned above. Alkoxy radicals chosen from alkoxycarbonyl groups may comprise, for example, from 1 to 4 carbon atoms. Acyl groups may comprise, for example, from 2 to 4 carbon atoms.

As used herein, "heterocycle" means, unless otherwise mentioned, an aromatic or non aromatic cycle comprising 5, 6 or 7 members, and from 1 to 3 heteroatoms chosen from nitrogen, sulphur and oxygen atoms. The heterocycles may be condensed on other heterocycles, or on other cyclic groups, for example, aromatic cyclic groups, such as a phenyl group. These heterocycles may also be quaternized by at least one alkyl radical. The terms alkyl and alkoxy have the meanings described above.

The heterocycles, for example, those of HET, may be chosen from thiophene, benzothiophene, furan, benzofuran, indole, indoline, carbazole, pyridine, dehydroquinoleine, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

As used herein, "aryl" means unless otherwise mentioned, an aryl radical comprising from $C_6$ to $C_{30}$ carbon atoms that may be substituted with at least one entity chosen from alkyl; alkoxy; acyl; cyano; carboxamido; —CO₂H; —SO₃H; —PO₃H₂; —PO₄H₂; hydroxyl; amino; monoalkyl ($C_1$–$C_4$)amino; and dialkyl($C_1$–$C_4$)amino radicals, in which the two alkyl groups can form, together with the nitrogen atom in the dialkyl($C_1$–$C_4$)amino group to which they are bonded, at least one cyclic group optionally interrupted by at least one atom chosen from nitrogen, oxygen and sulphur. For example, the aryl group may be chosen from phenyl and naphthyl that can be substituted as mentioned above.

The compounds of formulae (I) and (Ibis) may be defined as being direct dyes of the heteroyidiarylmethane type and the compounds of formulae (II), (IIbis) are leuco precursors of heteroyidiarylmethanes with formulae (I) and (Ibis).

The leuco compounds (II) or (IIbis) are usually only slightly colored or are not colored at all and can be transformed by simple oxidation in air or in the presence of an oxidizing agent into a heteroyldiarylmethane compound with formula (I) or (Ibis).

The at least one dye of formulae (I), (Ibis), (II), (IIbis) that may be used in dye compositions disclosed herein may, for example, be chosen from the following compounds, for which the counter ions are specified or not specified, and the addition salts thereof:

Methanaminium, N-[4-[[4-(dimethylamino)phenyl](2,2-dimethyl-2H-1-benzopyran-3-yl)methylene]-2,5-cyclohexadien-1-ylidene]-N-methyl-, acetate Methanaminium, N-[4-[[4-(dimethylamino)phenyl](2,2-dimethyl-2H-1-benzopyran-3-yl)methylene]-2,5-cyclohexadien-1-ylidene]-N-methyl- Methanaminium, N-[4-[[4-(dimethylamino)phenyl](2,2-dimethyl-2H-1-benzopyran-5-yl)methylene]-2,5-cyclohexadien-1-ylidene]-N-methyl-, acetate Methanaminium, N-[4-[[4-(dimethylamino)phenyl]2,2-dimethyl-2H-1-benzopyran-5-yl)methylene]-2,5-cyclohexadien-1-ylidene]-N-methyl- Methanaminium, N-[4-[[4-(dimethylamino)phenyl](2,2-dimethyl-2H-1-benzopyran-4-yl)methylene]-2,5-cyclohexadien-1-ylidene]-N-methyl-, acetate Methanaminium, N-[4-[[4-(dimethylamino)phenyl](2,2-dimethyl-2H-1-benzopyran-4-yl)methylene]-2,5-cyclohexadien-1-ylidene]-N-methyl- Methanaminium, N-[4-[[4-(dimethylamino)phenyl](2,2-dimethyl-2H-1-benzopyran-8-yl)methylene]-2,5-cyclohexadien-1-ylidene]-N-methyl-, acetate Methanaminium, N-[4-[[4-(dimethylamino)phenyl](2,2-dimethyl-2H-1-benzopyran-8-yl)methylene]-2,5-cyclohexadien-1-ylidene]-N-methyl- Methanaminium, N-[4-[[4-(dimethylamino)phenyl](2,2-dimethyl-2H-1-benzopyran-7-yl)methylene]-2,5-cyclohexadien-1-ylidene]-N-methyl-, acetate Methanaminium, N-[4-[[4-(dimethylamino)phenyl](2,2-dimethyl-2H-1-benzopyran-7-yl)methylene]-2,5-cyclohexadien-1-ylidene]-N-methyl- Methanaminium, N-[4-[[4-(dimethylamino)phenyl](2,2-dimethyl-2H-1-benzopyran-6-yl)methylene]-2,5-cyclohexadien-1-ylidene]-N-methyl-, acetate Methanaminium, N-[4-[[4-(dimethylamino)phenyl](2,2-dimethyl-2H-1-benzopyran-6-yl)methylene]-2,5-cyclohexadien-1-ylidene]-N-methyl- 2,5-Cyclohexadien-1-one, 4-[[4-amino-3,5-bis(1-methylethyl)phenyl](4-ethyl-3,4-dihydro-2H-1,4-benzoxazin-7-yl)methylene]-2,6-dimethoxy 2,5-Cyclohexadien-1-one, 4-[[3,4-dihydro-4-(2-pyridinylmethyl)-2H-1,4-benzoxazin-7-yl](4-ethyl-3,4-dihydro-2H-1,4-benzoxazin-7-yl)methylene]-2,6-dimethoxy- 2,5-Cyclohexadien-1-one, 4-[[4-(dimethylamino)phenyl](4-ethyl-3,4-dihydro-2H-1,4-benzoxazin-7-yl)methylene]-2,6-dimethoxy- 2,5-Cyclohexadien-1-one, 2,6-bis(1,1-dimethylethyl)-4-[(5-ethyl-2-thienyl)phenylmethylene]-

Ethanaminium, N-[3-carboxy-4-[[2-carboxy-4-[ethyl(2-methoxyethyl)amino]phenyl](7-carboxy-4-oxo-4H-1-benzothiopyran-3-yl)methylene]-2,5-cyclohexadien-1-ylidene]-N-ethyl-2-methoxy Ethanaminium, N-[4-[[4-[bis(2-methoxyethyl)amino]-2-carboxyphenyl](5-carboxy-2-pyridinyl)methylene]-3-carboxy-2,5-cyclohexadien-1-ylidene]-2-methoxy-N-(2-methoxyethyl)-

Ethanaminium, N-[4-[3-benzofuranyl[2-carboxy-4-[ethyl[2-(methylsulfonyl)amino]ethyl]amino]phenyl]methylene]-3-carboxy-2,5-cyclohexadien-1-ylidene]-N-ethyl-2-[(methylsulfonyl)amino]-, perchlorate Ethanaminium, N-[4-[3-benzofuranyl[2-carboxy-4-[ethyl[2-[(methylsulfonyl)amino]ethyl]amino]phenyl]methylene]-3-carboxy-2,5-cyclohexadien-1-ylidene]-N-ethyl-2-[(methylsulfonyl)amino]-

Ethanaminium, N-[4-[[4-[bis(2-methoxyethyl)amino]-2-carboxyphenyl](4-oxo-4H-1-benzothiopyran-3-yl)methylene]-3-carboxy-2,5-cyclohexadien-1-ylidene]-2-methoxy-N-(2-methoxyethyl)-, acetate Ethanaminium, N-[4-[[4-[bis(2-methoxyethyl)amino]-2-carboxyphenyl](4-oxo-4H-1-benzothiopyran-3-yl)methylene]-3-carboxy-2,5-cyclohexadien-1-ylidene]-2-methoxy-N-(2-methoxyethyl)-

Benzoic acid and 5-[(3-carboxy-4-oxo-2,5-cyclohexadien-1-ylidene)-3-pyridinylmethyl]-2-hydroxy-salt Methanaminium, N-[2-carboxy-4-[[3-carboxy-4-(dimethylamino)phenyl](4-oxo-4H-1-benzothiopyran-3-yl)methylene]-2,5-cyclohexadien-1-ylidene]-N-methyl-, perchlorate Methanaminium, N-[2-carboxy-4-[[3-carboxy-4-(dimethylamino)phenyl](4-oxo-4H-1-benzothiopyran-3-yl)methylene]-2,5-cyclohexadien-1-ylidene]-N-methyl- Benzoic acid and 5-[(3-carboxy-4-oxo-2,5-cyclohexadien-1-ylidene)[3,5-dimethyl-1-[2-[(methylsulfonyl)amino]ethyl]-1H-pyrazol-4-yl]methyl]-2-hydroxy-salt Benzoic acid and 5-[[2-[bis(2-methoxyethyl)amino ]-5-thiazolyl](3-carboxy-4-oxo-2,5-cyclohexadien-1-ylidene)methyl]-2-hydroxy-salt Ethanaminium, N-[4-[(7-carboxy-2-oxo-2H-1-benzopyran-4-yl)[4-(diethylamino)phenyl]methylene]-2,5-cyclohexadien-1-ylidene]-N-ethyl-, perchlorate Ethanaminium, N-[4-[(7-carboxy-2-oxo-2H-1-benzopyran-4-yl)[4-(diethylamino)phenyl]methylene]-2,5-cyclohexadien-1-ylidene]-N-ethyl- Ethanaminium, N-[4-[2-benzofuranyl [4-[ethyl[2-[(methylsulfonyl)amino]ethyl]amino]phenyl]methylene]-2,5-cyclohexadien-1-ylidene]-N-ethyl-2-[(methylsulfonyl)amino]-, perchlorate Ethanaminium, N-[4-[2-benzofuranyl[4-[ethyl[2-[(methylsulfonyl)amino]ethyl]amino]phenyl]methylene]-2,5-cyclohexadien-1-ylidene]-N-ethyl-2-[(methylsulfonyl)amino]-

Ethanaminium, N-[4-[(6-carboxybenzo[b]thien-2-yl)[4-(diethylamino)phenyl]methylene]-2,5-cyclohexadien-1-ylidene]-N-ethyl-, tetrafluoroborate(1-)

Ethanaminium, N-[4-[(6-carboxybenzo[b]thien-2-yl)[4-(diethylamino)phenyl]methylene]-2,5-cyclohexadien-1-ylidene]-N-ethyl- Ethanaminium, N-[4-[[5-[bis(2-methoxyethyl)amino]-2-furanyl][4-[ethyl[2-[(methylsulfonyl)amino]ethyl]amino]phenyl]methylene]-2,5-cyclohexadien-1-ylidene]-N-ethyl-2-[(methylsulfonyl)amino]-, perchlorate Ethanaminium, N-[4-[[5-[bis(2-methoxyethyl)amino]-2-furanyl][4-[ethyl[2-[(methylsulfonyl)amino]ethyl]amino]phenyl]methylene]-2,5-cyclohexadien-1-ylidene]-N-ethyl-2-[(methylsulfonyl)amino]-

2,5-Cyclohexadien-1-one, 4-[(4-hydroxyphenyl)-4-quinolinylmethylene]-

Ethanaminium, N-[4[[4-[Bis(2-methoxyethyl)amino]phenyl](7-carboxy-4-oxo-4H-1-benzopyran-3-yl)methylene]-2,5-cyclohexadien-1-ylidene]-2-methoxy-N-(2-methoxyethyl)-, sulfate (1:1)

Ethanaminium, N-[4-[[4-[bis(2-methoxyethyl)amino]phenyl](7-carboxy-4-oxo-4H-1-benzopyran-3-yl)methylene]-2,5-(cyclohexadien-1-ylidene]-2-methoxy-N-(2-methoxyethyl)-

Methanaminium, N-[4-[(5-carboxy-2-pyridinyl)[4-(dimethylamino)phenyl]methylene]-2,5-cyclohexadien-1-ylidene]-N-methyl-, perchlorate Methanaminium, N-[4-[(5-carboxy-2-pyridinyl)[4-(dimethylamino)phenyl]methylene]-2,5-cyclohexadien-1-ylidene]-N-methyl- 2-Thiophenecarboxylic acid, 5-[(4-hydroxyphenyl)(4-oxo-2,5-cyclohexadien-1-ylidene)methyl]

2,5-Cyclohexadien-1-one, 4-[2-furanyl(4-hydroxyphenyl)methylene]-

2,5-Cyclohexadien-1-one, 4-[(4-hydroxyphenyl)-2-pyridinylmethylene]-

Methanaminium, N-[3-carboxy-4-[[2-carboxy-4-(dimethylamino)phenyl](4-oxo-4H-1-benzopyran-3-yl)methylene]-2,5-cyclohexadien-1-ylidene]-N-methyl, perchlorate Methanaminium, N-[3-carboxy-4-[[2-carboxy-4-(dimethylamino)phenyl](4-oxo-4H-1-benzopyran-3-yl)methylene]-2,5-cyclohexadien-1-ylidene)-N-methyl- Ethanaminium, N-[4-[(5-carboxy-2-thienyl)[4-(diethylamino)phenyl]methylene]-2,5-cyclohexadien-1-ylidene]-N-ethyl-, perchlorate Ethanaminium, N-[4-[(5-carboxy-2-thienyl)[4-(diethylamino)phenyl]methylene]-2,5-cyclohexadien-1-ylidene]-N-ethyl- 2,5-Cyclohexadien-1-one, 4-[(4-methoxyphenyl)-3,6,9,12,15-pentaoxabicyclo[15,3,1]heneicosa-1(21),17,19-trien-21-ylmethylene]-3,6,9,12,15-Pentaoxabicyclo[15,3,1]heneicosane, 2,5-cyclohexadien-1-one Methanaminium, N-[4-[(2,3-dihydro-3-methyl-2-benzothiazolyl)[4-(dimethylamino)phenyl]methylene]-2,5-cyclohexadien-1-ylidene]-N-methyl-, chloride

[4-(α-Benzo[b]thien-2-yl-p-dimethylaminobenzylidene)-2,5-cyclohexadien-1-ylidene]dimethylammonium chloride

[4-(α-Benzo[b]thien-3-yl-p-dimethylaminobenzylidene)-2,5-cyclohexadien-1-ylidene]dimethylammonium chloride Methanaminium, N-[4-[[9-(dimethylamino)benzo[a]phenoxazin-7-ium-5-yl][4-dimethylamino)phenyl]methylene]-2,5-cyclohexadien-1-ydilene]-N-methyl-, bis[tetraphenylborate(1-)]

Methanaminium Benzo[a]phenoxazin-7-ium,

Methanaminium, N-[4-[[9(dimethylamino)benzo[a]phenoxazin-7-ium-5-yl][4-(dimethylamino)phenyl]methylene]-2,5-cyclohexadien-1-ydilene]-N-methyl-

[4-(α-3-Bromobenzo[b]thien-2-yl-p-dimethylamonobenzylidene)-2,5-cyclohexadien-1-ylidene]dimethylammonium chloride

[4-(α-3-Chlorobenzo[b]thien-2-yl-p-dimethylaminobenzylidene)-2,5-cyclohexadien-1ylidene]dimethylammonium chloride

[4-(p-Dimethylamino-α-3-methylbenzo[b]thien-2-ylbenzylidene)-2,5-cyclohexadien-1-ylidene]dimethylammonium chloride

[4-[2-Bromo-α-(p-dimethylaminophenyl)-3-thenylidene]-2,5-cyclohexadien-1-ylidene]dimethylammonium chloride

[4-[2-Chloro-α-(p-dimethylaminophenyl)-3-thenylidene]-2,5-cyclohexadien-1-ylidene]dimethylammonium chloride

[4-[α-(p-Dimethylaminophenyl)-3-thenylidene]-2,5-cyclohexadien-1-ylidene]dimethylammonium chloride

[4-[α-(p-Dimethylaminophenyl)-2,5-dimethyl-3-thenylidene]-2,5-cyclohexadien-1-ylidene]dimethylammonium chloride Pyridinium, 1-[[4-(dimethylamino)phenyl][4-(dimethyliminio)-2,5-cyclohexadien-1-ylidene]methyl]-, bis[tetrafluoroborate(1-)]

2,5-Cyclohexadien-1-one, 2,3,5,6-tetrachloro-4-[(pentachlorophenyl)(2,3,5,6-tetrachloro-4-pyridinyl)methylene]-

Ethanaminium, N-[4-[[4-(diethylamino)phenyl](4-oxo-4H-1-benzothiopyran-3-yl)methylene]-2,5-cyclohexadien-1-ylidene]-N-ethyl-, perchlorate Ethanaminium, N-[4-[[4-(diethylamino)phenyl](4-oxo-4H-1-benzothiopyran-3-yl)methylene]-2,5-cyclohexadien-1-ylidene]-N-ethyl- 4H-1-Benzothiopyran, ethanaminium deriv, Benzenaminium, N-methyl-N-[4-[[4-methylphenylamino)phenyl](4-oxo-4H-1-benzothiopyran-3-yl)methylene]-2,5-cyclohexadien-1-ylidene]-, perchlorate Benzenaminium, N-methyl-N-[4-[[4-methylphenylamino)phenyl](4-oxo-4H-1-benzothiopyran-3-yl)methylene]-2,5-cyclohexadien-1-ylidene]-

Ethanaminium, N-[4-[[4-(diethylamino)-2-methylphenyl](4-oxo-4H-1-benzothiopyran-3-yl)methylene]-3-methyl-2,5-cyclohexadien-1-ylidene]-N-ethyl, perchlorate Ethanaminium, N-[4-[[4-(diethylamino)-2-methylphenyl](4-oxo-4H-1-benzothiopyran-3-yl)methylene]-3-methyl-2,5-cyclohexadien-1-ylidene]-N-ethyl- Ethanaminium 4H-1-Benzothiopyran, Methanaminium, N-[4-[[4-(dimethylamino)phenyl][5-(4-iodophenyl)-2-furanyl]methylene]-2,5-cyclohexadien-1-ylidene]-N-methyl-, chloride Methanaminium, N-[4-[[5-(4-bromophenyl)-2-furanyl][4(dimethylamino)phenyl]methylene]-2,5-cyclohexadien-1-ylidene]-N-methyl-, chloride Methanaminium, N-[4-[[4-(dimethylamino)phenyl][5-(4-nitrophenyl)-2-furanyl]methylene]-2,5-cyclohexadien-1-ylidene]-N-methyl-, chloride

[Oxybis[methylene-5,2-furandiyl[p-(N-methylanilino)benzylidyne-2,5-cyclohexadien-4,1-diylidene)]bis[methylphenylammonium chloride]

[Oxybis[methylene-5,2-furandiyl[p-(N-methylanilino)benzylidyne-2,5-cyclohexadien-4,1-diylidene]]bis[methylphenylammonium hydrogenosulfate]

Benzenaminium, N,N'-[oxybis[methylene-5,2-furandiyl[[4(methylphenylamino)phenyl]methylidyne]-2,5-cyclohexadien-4,1-diylidene]]bis[N-methyl- 1,4-Cyclohexadien-1-sulfonic acid and, 3-[4-anilino-α-(1-methyl-2-phenylindol-3-yl)-3-sulfobenzylidene]-6-phenylimino-salt Trifluoromethane sulfonic acid and Pyridinium, 1-[[4(dimethylamino)phenyl][4-(dimethyliminio)-2,5-cyclohexadien-1-ylidene]methyl salt Trifluoromethane sulfonic acid and 1-[[4-(dimethylamino)phenyl][4-dimethyliminio)-2,5-cyclohexadien-1-ylidene]methyl]pyridinium salt Pyridinium, 1-[[4-(dimethylamino)phenyl][4-(dimethyliminio)-2,5-cyclohexadien-1-ylidene]methyl]-

[4-(p-(Dimethylamino)-α-(9-methylcarbazol-3-yl)benzylidene]-2,5-cyclohexadien-1-ylidene]dimethylammonium chloride

[4-[α-[p-(Dimethylamino)phenyl]furfurylidene]-2,5-cyclohexadien-1-ylidene]dimethylammonium chloride Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-, perchlorate, diperchlorate Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-, perchlorate Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-1H-Indolizinium, 3-[[4-(dimethyliminio)-2,5-cyclohexadien-1-ylidene](4-methoxyphenyl)methyl]-2-(2-hydroxy-5-methylphenyl)-1-methyl-, 1H-Indolizinium, 3-[[4-(dimethyliminio)-2,5-cyclohexadien-1-ylidene]phenylmethyl]-2-(2-hydroxy-5-methylphenyl)-1-methyl-, 1H-Indolizinium, 3-[[4-(dimethylamino)phenyl][4-(dimethyliminio)-2,5-cyclohexadien-1-ylidene]methyl-2-(2-hydroxy-5-methylphenyl)-1-methyl-, 1H-Indolizinium, 3-[[4-(dimethylamino)phenyl][4-(dimethyliminio)-2,5-cyclohexadien-1-ylidene]methyl]-2-(2-hydroxy-5-methylphenyl)-1-methyl- 1(Propanaminium, N-[4-[2-benzofuranyl[3-chloro-4-[ethyl(3-sulfopropyl)amino]phenyl]methylene]-2-chloro-2,5-cyclohexadien-1-ylidene]-N-ethyl-3-sulfo-, internal salt, sodium salt 1-Propanaminium, N-[4-[2-benzofuranyl[4-[ethyl(3-sulfopropyl)amino]-3-methylphenyl]methylene]-2-methyl-2,5-cyclohexadien-1-ylidene]-N-ethyl-3-

1-Butanaminium, N-[4-[2-benzofuranyl[4-[ethyl(4-sulfobutyl)amino]phenyl]methylene]-2,5-cyclohexadien-1-ylidene]-N-ethyl-4-

1-Propanaminium, N-[4-[(5-chlorobenzo[b]thien-2-yl)[4-[methyl(3-sulfopropyl)amino]phenyl]methylene]-2,5-cyclohexadien-1-ylidene]-N-methyl-3-sulfo-, 1-Propanaminium, N-[4-[(3-chlorobenzo[b]thien-2-yl)[4-[methyl(3-sulfopropyl)amino]phenyl]methylene]-2,5-cyclohexadien-1-ylidene]-N-methyl-3-sulfo, sodium salt 1-Propanaminium, N-[4-[Benzo[b]thien-2-yl[4-[methyl(3-sulfopropyl)amino]phenyl]methylene]-2,5-cyclohexadien-1-ylidene]-N-methyl-3-sulfo-, sodium salt 1-Propanaminium, N-methyl-N-[4-[(3-methylbenzo[b]thien-2-yl)[4-[methyl(3-sulfopropyl)amino]phenyl]methylene]-2,5-cyclohexadien-1-ylidene]-3-sulfo-, sodium salt 1-Propanaminium, N-[4-[(3-bromobenzo[b]thien-2-yl)[4-[methyl(3-sulfopropyl)amino]phenyl]methylene]-2,5-cyclohexadien-1-ylidene]-N-methyl-3-sulfo-, sodium salt 1-Propanaminium, N-[4-[(6-chlorobenzo[b]thien-2-yl)[4-[methyl(3-sulfopropyl)amino]phenyl]methylene]-2,5-cyclohexadien-1-ylidene]-N-methyl-3-sulfo-, sodium salt 1-Propanaminium, N-methyl-N-[4-[[4-[methyl(3-sulfopropyl)amino]phenyl](5-nitro-2-benzofuranyl)methylene]-2,5-cyclohexadien-1-ylidene]-3-sulfo-, sodium salt 1-Propanaminium, N-methyl-N-[4-[(5-methyl-2-benzofuranyl)[4-(methyl(3-sulfopropyl)amino]phenyl]methylene]-2,5-cyclohexadien-1-ylidene]-3-sulfo-, sodium salt 1-Propanaminium, N-[4-[(5-chloro-2-benzofuranyl)[4-[methyl(3-sulfopropyl)amino]phenyl]methylene]-2,5-cyclohexadien-1-ylidene]-N-methyl-3-sulfo-, sodium salt 1-Propanaminium, N-[4-[2-benzofuranyl[4-[methyl(3-sulfopropyl)amino]phenyl]methylene]-2,5-cyclohexadien-1-ylidene]-N-methyl-3-sulfo-, internal salt, sodium salt Ethanaminium, N-[4-[(2-chlorophenyl)(1-methyl-2-phenyl-1H-indol-3-yl)methylene]-2,5-cyclohexadien-1-ylidene]-N-ethyl-, trichlorozincate(1-)

Zincate(1-), trichloro-, N-[4-[(2-chlorophenyl)(1-methyl-2-phenyl-1H-indol-3-yl)methylene]-2,5-cyclohexadien-1-ylidene]-N-ethylethanaminium Benzenesulfonic acid, 5-[(1,2-dimethyl-1H-indol-3-yl)[4-[(2-methylphenyl)imino]-3-sulfo-2,5-cyclohexadien-1-ylidene]methyl]-2-[(2-methylphenyl)amino]-, monosodium salt Ethanaminium, N-[4-[(2-chlorophenyl)(1-methyl-2-phenyl-1H-indol-3-yl)methylene]-2,5-cyclohexadien-1-ylidene]-N-ethyl-, methyl sulfate 3H-Pyrazol-3-one, 1,2-dihydro-4-[(4-hydroxy-3-methoxyphenyl)(3-methoxy-4-oxo-2,5-cyclohexadien-1-ylidene)methyl]-1,5-dimethyl-2-phenyl-, ion(1-)

Ethanaminium, N-[4-[(2-chlorophenyl)(1-methyl-2-phenyl-1H-indol-3-yl)methylene]-2,5-cyclohexadien-1-ylidene]-N-ethyl-, acetate Ethanaminium, N-[4-[(2-chlorophenyl)(1-methyl-2-phenyl-1H-indol-3-yl)methylene]-2,5-cyclohexadien-1-ylidene]-N-ethyl-, phosphate (1:1)

Ethanaminium, N-[4-[(2-chlorophenyl)(1-methyl-2-phenyl-1H-indol-3-yl)methylene]-2,5-cyclohexadien-1-ylidene]-N-ethyl- Ethanaminium, N-[4-[(2-chlorophenyl)(1-methyl-2-phenyl-1H-indol-3-yl)methylene]-2,5-cyclohexadien-1-ylidene]-N-ethyl-, chloride, compound with zinc chloride ($ZnCl_2$)

N-[4-[(2-chlorophenyl)(1-methyl-2-phenyl-1H-indol-3-yl)methylene]-2,5-cyclohexadien-1-ylidene]-N-ethylethanaminium chloride 1-Piperidinyloxy, 4-[[3,5-bis(1,1-dimethylethyl)-4-oxo-2,5-cyclohexadien-1-ylidene][3,5-bis(1,1-dimethylethyl)-4-oxyphenyl]methyl]-2,2,6,6-tetramethyl-1H-Pyrrol-1-yloxy, 3-[[3,5-bis(1,1-dimethylethyl)-4-oxo-2,5-cyclohexadien-1-ylidene][3,5-bis(1,1-dimethylethyl)-4-oxyphenyl]methyl]-2,5-dihydro-2,2,5,5-tetramethyl- 1H-Pyrrol-1-yloxy, 3-[[3,5-bis(1,1-dimethylethyl)-4-hydroxyphenyl][3,5-bis(1,1-dimethylethyl)-4-oxo-2,5-cyclohexadien-1-ylidene]methyl]-2,5-dihydro-2,2,5,5-tetramethyl- 1-Pyperidinyloxy, 4-[[3,5-bis(1,1-dimethylethyl)-4-hydroxyphenyl][3,5-bis(1,1-dimethylethyl)-4-oxo-2,5-cyclohexadien-1-ylidene]methyl]-2,2,6,6-tetramethyl- Acetamide, N-methyl-N-[[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-

Carbamic acid [[2-[(3,5-dimethoxy-4-oxo-2,5-cyclohexadien-1-ylidene)(2,3,6,7-tetrahydro-1H,5H-benzo[ij]quinolizin-9-yl)methyl]phenyl]sulfonyl]methyl-, 2-(methylsulfonyl)ethyl ester Carbamic acid methyl[[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-, 2-cyanoethyl ester Carbamic acid methyl [[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-, 2-(methylsulfonyl)ethylester Carbamic acid methyl [[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-, 2-(phenylsulfonyl)ethyl ester Acetamide, N-[[2-[(3,5-dimethyl-4-oxo-2,5-cyclohexadien-1-ylidene)(2,3,6,7-tetrahydro-1H,5H-benzo[ij]quinolizin-9-yl)methyl]phenyl]sulfonyl]-N-methyl-2,5-Cyclohexadien-1-one, 4-[(4-hydroxy-3,5-dimethylphenyl)(2,3,5,6,8,9,11,12-octahydro-1,4,7,10,13-benzopentaoxacyclopentadecin-15-yl)methylene]-2,6-dimethyl- Phenoxy, 4-[[3,5-bis(1,1-dimethylethyl)-4-oxo-2,5-cyclohexadien-1-ylidene](2,3,5,6,8,9,11,12-octahydro-1,4,7,10,13-benzopentaoxacyclopentadecin-15-yl)methyl]-2,6-bis(1,1-dimethylethyl)-

Ethanaminium, N-[4-[(2-chlorophenyl)(1-methyl-2-phenyl-1H-indol-3-yl)methylene]-2,5-cyclohexadien-1-ylidene]-N-ethyl-, chloride Phenoxy, 4-[[3,5-bis(1,1-dimethylethyl)-4-oxo-2,5-cyclohexadien-1-ylidene]-3-pyridinylmethyl]-2,6-bis(1,1-dimethylethyl)-

2,5-Cyclohexadien-1-one, 4-[[3,5-bis(1,1-dimethylethyl)-4-hydroxyphenyl]-3-pyridinylmethylene]-2,6-bis(1,1-dimethylethyl)-, ion(1-)

2,5-Cyclohedaxien-1-one, 4-[[3,5-bis(1,1-dimethylethyl)-4-hydroxyphenyl]-3-pyridinylmethylene]-2,6-bis(1,1-dimethylethyl)-

Phenoxy, 4,4'-[3,5-pyridinediylbis[[3,5-bis(1,1-dimethylethyl)-4-oxo-2,5-cyclohexadien-1-ylidene]methylene]]bis[2,6-bis(1,1-dimethylethyl)-

Phenoxy, 4,4'-[2,4-pyridinediylbis[[3,5-bis(1,1-dimethylethyl)-4-oxo-2,5-cyclohexadien-1-ylidene]methylene]]bis(2,6-bis(1,1-dimethylethyl)-

Phenoxy, 4,4'-[2,5-pyridinediylbis[[3,5-bis(1,1-dimethylethyl)-4-oxo-2,5-cyclohexadien-1-ylidene]methylene]]bis[2,6-bis(1,1-dimethylethyl)-

Methanaminium, N-[4-[9H-carbazol-3-yl[4-(dimethylamino)phenyl]methylene]-2,5-cyclohexadien-1-ylidene]-N-methyl-, chloride

[4-[α-Carbazol-3-yl-p-(dimethylamino)benzylidene]-2,5-cyclohexadien-1-ylidene]dimethylammonium chloride Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene]-, acetate Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene]-(2,5-Cyclohexadien-1-one, 4,4'-[3,5-pyridinediylbis[(3,5-bis(1,1-dimethylethyl)-4-hydroxyphenyl]methylidyne]]bis[2,6-bis(1,1-dimethylethyl)-, ion(2-)-

2,5-Cyclohexadien-1-one, 4,4'-[2,6-pyridinediylbis[[3,5-bis(1,1-dimethylethyl)-4-hydroxyphenyl]methylidyne]]bis[2,6-bis(1,1-dimethylethyl)-, ion(2-)-

2,5-Cyclohexadien-1-one, 4,4'-[2,5-pyridinediylbis[[3,5-bis(1,1-dimethylethyl)-4-hydroxyphenyl]methylidyne]]bis[2,6-bis(1,1-dimethylethyl)-, ion(2-)-

2,5-Cyclohexadien-1-one, 4,4'-[2,4-pyridinediylbis[[3,5-bis(1,1-dimethylethyl)-4-hydroxyphenyl]methylidyne]]bis[2,6-bis(1,1-dimethylethyl)-, ion(2-)-

2,5-Cyclohexadien-1-one, 4,4'-[3,5-pyridinediylbis[[3,5-bis(1,1-dimethylethyl)-4-hydroxyphenyl]methylidyne]]bis[2,6-bis(1,1-dimethylethyl)-

2,5-Cyclohexadien-1-one, 4,4'-[2,5-pyridinediylbis[[3,5-bis(1,1-dimethylethyl)-4-hydroxyphenyl]methylidyne]]bis[2,6-bis(1,1-dimethylethyl)-

2,5-Cyclohexadien-1-one, 4,4'-[2,4-pyridinediylbis[[3,5-bis(1,1-dimethylethyl)-4-hydroxyphenyl]methylidyne]]bis[2,6-bis-1,1-dimethylethyl)-

Cyclohexanaminium, N-methyl-N-[4-[(2-methyl-1H-indol-3-yl)phenylmethylene]-2,5-cyclohexadien-1-ylidene]-, trichlorozincate(1-)

Zincate(1-), trichloro-, N-methyl-N-[4-[(2-methyl-1H-indol-3-yl)phenylmethylene]-2,5-cyclohexadien-1-ylidene] cyclohexanaminium Cyclohexanaminium, N-methyl-N-[4-[(2-methyl-1H-indol-3-yl)phenylmethylene]-2,5-cyclohexadien-1-ylidene]-

Cyclohexanaminium, N-[4-[(2-chlorophenyl)(1-methyl-2-phenyl-1H-indol-3-yl)methylene]-2,5-cyclohexadien-1-ylidene]-N-methyl-, trichlorozincate(1-)

Zincate(1-), trichloro-, N-[4-[(2-chlorophenyl)-(1-methyl-2-phenyl-1H-indol-3-yl)methylene]-2,5-cyclohexadien-1-ylidene]-N-methylcyclohexanaminium Cyclohexanaminium, N-[4-[(2-chlorophenyl)(1-methyl-2-phenyl-1H-indol-3yl)methylene]-2,5-cyclohexadien-1-ylidene]-N-methyl- Cyclohexanaminium, N-[4-[(2-chlorophenyl)[2-(4-chlorophenyl)-1-methyl-1H-indol-3-yl]methylene]-2,5-cyclohexadien-1-ylidene]-N-methyl-, trichlorozincate(1-)

N-[4-[(2-chlorophenyl)[2-(4-chlorophenyl)-1-methyl-1H-indol-3-yl]methylene]-2,5-cyclohexadien-1-ylidene]-N-methylcyclohexanaminium trichlorozincate Cyclohexanaminium, N-[4-[(2-chlorophenyl)[2-(4-chlorophenyl)-1-methyl-1H-indol-3-yl]methylene]-2,5-cyclohexadien-1-ylidene]-N-methyl- Benzenemethanaminium, N-cyclohexyl-N-[4-[[1-(2-ethoxyethyl)-2-phenyl-1H-indol-3-yl](4-methylphenyl)methylene]-2,5-cyclohexadien-1-ylidene]-, trichlorozincate(1-)

N-cyclohexyl-N-[4-[[1-(2-ethoxyethyl)-2-phenyl-1H-indol-3-yl](4-methylphenyl)methylene]-2,5-cyclohexadien-1-ydilene]benzenemethanaminium trichlorozincate Benzenemethanaminum, N-cyclohexyl-N-[4-[[1-(2-ethoxyethyl)-2-phenyl-1H-indol-3-yl](4-methylphenyl)methylene]-2,5-cyclohexadien-1-ylidene]-

Cyclohexanaminium, N-methyl-N-[4[(1-methyl-2-phenyl-1H-indol-3-yl)phenylmethylene]-2,5-cyclohexadien-1-ylidene]-, trichlorozincate(1-)

N-methyl-N[4-[(1-methyl-2-phenyl-1H-indol-3-yl)phenylmethylene]-2,5-cyclohexadien-1-ylidene]cyclohexanaminium trichlorozincate Cyclohexanaminium, N-methyl-N-[4-[(1-methyl-2-phenyl-1H-indol-3-yl)phenylmethylene]2,5-cyclohexadien-1-ylidene]-

Cyclohexanaminium, N-[4-[(2-bromophenyl)(1,2-dimethyl-1H-indol-3-yl)methylene]-2,5-cyclohexadien-1-ylidene]-N-ethyl-, trichlorozincate(1-)

N-[4-[(2-bromophenyl)(1,2-dimethyl-1H-indol-3-yl)methylene]-2,5-cyclohexadien-1-ylidene]-N-ethylcyclohexanaminium trichlorozincate Cyclohexanaminium, N-[4-[(2-bromophenyl)(1,2-dimethyl-1H-indol-3-yl)methylene]-2,5-cyclohexadien-1-ylidene]-N-ethyl- Ethanaminium, N-[3-chloro-4-[(1-methyl-2-phenyl-1H-indol-3-yl)phenylmethylene]-2,5-cyclohexadien-1-ylidene]-N-ethyl-, sulfate (1:1)

Ethanaminium, N-[3-chloro-4-[(1-methyl-2-phenyl-1H-indol-3-yl)phenylmethylene]-2,5-cyclohexadien-1-ylidene]-N-ethyl- Ethanaminium, N-ethyl-N-[4-[(2-methyl-1H-indol-3-yl)(2-nitrophenyl)methylene]-2,5-cyclohexadien-1-ylidene]-, sulfate (1:1)

Ethanaminium, N-ethyl-N-[4-[(2-methyl-1H-indol-3-yl)(2-nitrophenyl)methylene]-2,5-cyclohexadien-1-ylidene]-

Methanamine, N-[4-[(1-methyl-2-phenyl-1H-indol-3-yl)phenylmethylene]-2,5-cyclohexadien-1-ylidene]-, sulfate (1:1)

Methanamine, N-4-[(1-methyl-2-phenyl-1H-indol-3-yl)phenylmethylene]-2,5-cyclohexadien-1-ylidene]-

Methanaminium, N-[4-[[4-(dimethylamino)phenyl]-2-furanylmethylene]-2,5-cyclohexadien-1-ylidene]-N-methyl-, (T-4)-tetrabromothallate(1-)

Thallate(1-), tetrabromo-, (T-4), N-[4-[[4-(dimethylamino)phenyl]-2-furanylmethylene]-2,5-cyclohexadien-1-ylidene]-N-methylmethanaminium Phenoxy, 4-[[3,5-bis(1,1-dimethylethyl)-4-oxo-2,5-cyclohexadien-1-ylidene][6-[[3,5-bis(1,1-dimethylethyl)-4-oxo-2,5-cyclohexadien-1-ylidene][3,5-bis(1,1-dimethylethyl)-4-4,4'-[2,6-pyridinediylbis[[3,5-bis (1,1-dimethylethyl)-4-hydroxyphenyl]methylidyne]]bis[2,6-bis(1,1-dimethylethyl)-

Methanaminium, N-[4-[(2,3-dihydro-1,5-dimethyl-3-oxo-2-phenyl-1H-pyrazol-4-yl)(3-nitrophenyl)methylene]-2,5-cyclohexadien-1-ylidene]-N-methyl-, chloride Methanaminium, N-[4-[(3-bromophenyl)(2,3-dihydro-1,5-dimethyl-3-oxo-2-phenyl-1H-pyrazol-4-yl)methylene]-2,5-cyclohexadien-1-ylidene]-N-methyl-, chloride Methanaminium, N-[4-[(2,3-dihydro-1,5-dimethyl-3-oxo-2-phenyl-1H-pyrazol-4-yl)(3-methoxyphenyl)methylene]-2,5-cyclohexadien-1-ylidene]-N-methyl-, chloride Methanaminium, N-[4-[(2,3-dihydro-1,5-dimethyl-3-oxo-2-phenyl-1H-pyrazol-4-yl)phenylmethylene]-2,5-cyclohexadien-1-ylidene]-N-methyl-, chloride [[4-[(1-methyl-2-phenyl-1H-indol-3-yl)[4-[(sulfophenyl)amino]phenyl]methylene]-2,5-cyclohexadien-1-ylidene]amino]-

Methanaminium, N-[4-[(2,3-dihydro-1,5-dimethyl-3-oxo-2-phenyl-1H-pyrazol-4-yl)[4-(dimethylamino)phenyl]methylene]-2,5-cyclohexadien-1-ydilene]-N-methyl-, chloride Benzenamine, 4-[(2-[1,1'-biphenyl]-4-yl-1-butyl-1H-indol-3-yl)[4-[(4-ethoxyphenyl)imino]-2,5-cyclohexadien-1-ylidenemethyl]-N-(4-ethoxyphenyl)-

Benzenaminium, N-methyl-N-[4-[[4-(methylphenylamino)phenyl](4-oxo-4H-1-benzopyran-3-yl)methylene]-2,5-cyclohexadien-1-ylidene]-

Ethanaminium, N-[4-[[4-(diethylamino)phenyl](4-oxo-4H-1-benzopyran-3-yl)methylene]-2,5-cyclohexadien-1-ylidene]-N-ethyl- Benzenaminium, 4-ethoxy-N-methyl-N-[4-[(1-methyl-2-phenyl-1H-indol-3-yl)phenylmethylene]-2,5-cyclohexadien-1-ylidene], chloride Methanaminium, N-[4-[12H-benzo[a]phenoxazin-5-yl[4-(dimethylamino)phenyl]methylene]-2,5-cyclohexadien-1-ylidene]-N-methyl-, chloride Benzenaminium, N-methyl-N-[4-[(1-methyl-2-phenyl-1H-indol-3-yl)phenylmethylene]-2,5-cyclohexadien-1-ylidene]-

Ethanaminium, N-[4-[[4-(diethylamino)phenyl](7-methoxy-2,1,3-benzothiadiazol-4-yl)methylene]-2,5-cyclohexadien-1-ylidene]-N-ethyl- Ethanaminium, N-[4-[[4-(diethylamino)phenyl](5-methoxy-2,1,3-benzothiadiazol-4-yl)methylene]-2,5-cyclohexadien-1-ylidene]-N-ethyl- Ethanaminium, N-[4-[[4-(diethylamino)phenyl](7-methyl-2,1,3-benzothiadiazol-4-yl)methylene]-2,5-cyclohexadien-1-ylidene]-N-ethyl- Ethanaminium, N-[4-[2,1,3-benzothiadiazol-5-yl[4-(diethylamino)phenyl]methylene]-2,5-cyclohexadien-1-ylidene]-N-ethyl- Ethanaminium, N-[4-[2,1,3-benzothiadiazol-4-yl[4-(diethylamino)phenyl]methylene]-2,5-cyclohexadien-1-ylidene]-N-ethyl- Methanaminium, N-methyl-N-[4-[(1-methyl-2-phenyl-1H-indol-3-yl)phenylmethylene]-2,5-cyclohexadien-1-ylidene]-, chloride Methanaminium, N-methyl-N-[4-[(1-methyl-2-phenyl-1H-indol-3-yl)phenylmethylene]-2,5-cyclohedaxien-1-ylidene]-

Methanaminium, N-[4-[[4-(dimethylamino)phenyl](7-methoxy-2,1,3-benzothiadiazol-4-yl)methylene]-2,5-cyclohexadien-1-ylidene]-N-methyl- Methanaminium, N-[4-[[4-(dimethylamino)phenyl](5-methoxy-2,1,3-benzothiadiazol-4-yl)methylene]-2,5-cyclohexadien-1-ylidene]-N-methyl- Methanaminium, N-[4-[[4-(dimethylamino)phenyl](7-methyl-2,1,3-benzothiadiazol-4-yl)methylene]-2,5-cyclohexadien-1-ylidene]-N-methyl- Methanaminium, N-[4-[2,1,3-benzothiadiazol-5-yl[4-dimethylamino)phenyl]methylene]-2,5-cyclohexadien-1-ylidene]-N-methyl- Methanaminium, N-[4-[2,1,3-benzothiadiazol-4-yl[4-(dimethylamino)phenyl]methylene]-2,5-cyclohexadien-1-ylidene]-N-methyl- Methanaminium, N-[4-[[4-(dimethylamino)phenyl]-3-pyridinylmethylene]-2,5-cyclohexadien-1-ylidene]-N-methyl- Methanaminium, N-[4-[[4-(dimethylamino)phenyl]-4-pyridinylmethylene]-2,5-cyclohexadien-1-ylidene]-N-methyl- Methanaminium, N-[4-[[4-(dimethylamino)phenyl]-2-thienylmethylene]-2,5-cyclohexadien-1-ylidene]-N-methyl- Methanaminium, N-[4-[[4-(dimethylamino)phenyl]-2-furanylmethylene]-2,5-cyclohexadien-1-ylidene]-N-methyl- Methanaminium, N-[4-[[4-(dimethylamino)phenyl]-3-thienylmethylene]-2,5-cyclohexadien-1-ylidene]-N-methyl-
[[4-[(1-methyl-2-phenyl-1H-indol-3-yl)[4-[(sulfophenyl)amino]phenyl]methylene]-2,5-cyclohexadien-1-ylidene]amino]-, Ethoxy [[4-[[-4[(ethoxysulfophenyl)amino]phenyl](1-methyl-2-phenyl-1H-indol-3-yl)methylene]-2,5-cyclohexadien-1-ylidene]amino]-

Benzenamine, N-methyl-4-[[4-(methylimino)-2,5-cyclohedaxien-1-ylidene](2-methyl-1H-indol-3-yl)methyl]-, Methanaminium, N-[4-[[4-(dimethylamino)phenyl](2-methyl-1H-indol-3-yl)methylene]-2,5-cyclohexadien-1-ylidene]-N-methyl-, Benzenamine, N-methyl-4-[[4-(methylimino)-2,5-cyclohexadien-1-ylidene](1-methyl-2-phenyl-1H-indol-3-yl)methyl]-, conjugated monoacid Methanaminium, N-[4-[[4-(dimethylamino)phenyl](1-methyl-2-phenyl-1H-indol-3-yl)methylene]-2,5-cyclohexadien-1-ylidene]-N-methyl- Benzenamine, 4-ethoxy-N-[4-[[4-[(4-ethoxyphenyl)amino]phenyl](2-phenyl-1H-indol-3-yl)methylene]-2,5-cyclohexadien-1-ylidene]-, Benzenamine, 4-ethoxy-N-[4-[[4-[(4-ethoxyphenyl)amino]phenyl](2-methyl-1H-indol-3-yl)methylene]-2,5-cyclohexadien-1-ylidene]-, Benzenamine, N-[4-[(1,2-dimethyl-1H-indol-3-yl)[4-[(4-ethoxyphenyl)amino]phenyl]methylene]-2,5-cyclohexadien-1-ylidene]-4-ethoxy- Benzenamine, 4-[(1-methyl-2-phenyl-1H-indol-3-yl)[4-(phenylimino)-2,5-cyclohexadien-1-ylidene]methyl]-N-phenyl-, conjugated monoacid Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene]-, Methanaminium, N-[4-[[4-(dimethylamino)phenyl](2-phenyl-1H-indol-3-yl)methylene]-2,5-cyclohexadien-1-ylidene]-N-methyl- Benzenaminium, N-methyl-N-[4-[[4-(methylphenylamino)phenyl](4-oxo-4H-1-benzopyran-3-yl)methylene]-2,5-cyclohexadien-1-ylidene]-, chloride Benzenaminium, N-methyl-N-[4-[[4-(methylphenylamino)phenyl](4-oxo-4H-1-benzopyran-3-yl)methylene]-2,5-cyclohexadien-1-ylidene]-, perchlorate Ethanaminium, N-[4-[[4-(diethylamino)phenyl](4-oxo-4H-1-benzopyran-3-yl)methylene]-2,5-cyclohexadien-1-ylidene]-N-ethyl-, perchlorate Ethanaminium, N-[4-[[4-(diethylamino)phenyl](4-oxo-4H-1-benzopyran-3-yl)methylene]-2,5-cyclohexadien-1-ylidene]-N-ethyl-, chloride Benzenaminium, N-methyl-N-[4-[[4-(methylphenylamino)phenyl](4-oxo-4H-1-benzopyran-3-yl)methylene]-2,5-cyclohexadien-1-ylidene]-, acetate Ethanaminium, N-[4-[[4-(diethylamino)phenyl](4-oxo-4H-1-benzopyran-3-yl)methylene]-2,5-cyclohexadien-1-ylidene]-N-ethyl-, acetate Methanaminium, N-[4-[(2,3-dihydro-1,5-dimethyl-3-oxo-2-phenyl-1H-pyrazol-4-yl)(3-nitrophenyl)methylene]-2,5-cyclohexadien-1-ylidene]-N-methyl- Methanaminium, N-[4-[(3-bromophenyl)(2,3-dihydro-1,5-dimethyl-3-oxo-2-phenyl-1H-pyrazol-4-yl)methylene]-2,5-cyclohexadien-1-ylidene]-N-methyl- Methanaminium, N-[4-[(2,3-dihydro-1,5-dimethyl-3-oxo-2-phenyl-1H-pyrazol-4-yl)(3-methoxyphenyl)methylene]-2,5-cyclohexadien-1-ylidene]-N-methyl- Methanaminium, N-[4-[(2,3-dihydro-1,5-dimethyl-3-oxo-2-phenyl-1H-pyrazol-4-yl)phenylmethylene]-2,5-cyclohexadien-1-ylidene]-N-methyl- Methanaminium, N-[4-[(2,3-dihydro-1,5-dimethyl-3-oxo-2-phenyl-1H-pyrazol-4-yl)(3-methylphenyl)methylene]-2,5-cyclohexadien-1-ylidene]-N-methyl- Benzenamine, N-[4-[(1-ethyl-2-phenyl-1H-indol-3-yl)[4-[(2-methoxyphenyl)amino]phenyl]methylene]-2,5-cyclohexadien-1-ylidene]-2-methoxy-, monochlorhydrate 2-hydroxy-5-[[4-[[4-[(4-hydroxy-3-sulfophenyl)amino]phenyl](1-methyl-2-phenyl-1H-indol-3-yl)methylene]-2,5-cyclohexadien-1-ylidene]amino]-

Benzenamine, 2-ethoxy-N-[4-[[4-(2-ethoxyphenyl)amino]phenyl](1-methyl-2-phenyl-1H-indol-3-yl)methylene]-2,5-cyclohexadien-1-ylidene]-, monochlorhydrate Methanaminium, N-[4-[[4-(dimethylamino)phenyl]-2-furanylmethylene]-2,5-cyclohexadien-1-ylidene]-N-methyl-, perchlorate 2-ethoxy-5-[[4-[[4-[(4-ethoxy-3-sulfophenyl)amino]phenyl](1-methyl-2-phenyl-1H-indol-3-yl)methyl]-2,5-cyclohexadien-1-ylidene]amino]-

Ammonium, [4-[α-[p-(dimethylamino)phenyl]furfurylidene]-2,5-cyclohexadien-1-ylidene]dimethyl-, tetrachlorogallate(1-)

Methanaminium, N-[4-[[4-(dimethylamino)phenyl]-2-thienylmethyl]-2,5-cyclohexadien-1-ylidene]-N-methyl-, perchlorate Ammonium, [4-[p-(dimethylamino)-α-2-thienylbenzylidene]-2,5-cyclohexadien-1-ylidene]dimethyl-, perchlorate Ammonium, (2-cyanoethyl)[4-[α-[4-[(2-cyanoethyl)ethylamino]-α-tolyl]piperonylidene]-3-methyl-2,5-cyclohexadien-1-ylidene]ethyl- Ammonium, dimethyl[4-[α-(1-methyl-2-phenylindol-3-yl)benzylidene]-2,5-cyclohexadien-1-ylidene]-, chloride, Ammonium, (p-ethoxyphenyl)methyl[4-[α-(1-methyl-2-phenylindol-3-yl)benzylidene]-2,5-cyclohexadien-1-ylidene]-, chloride, (p-ethoxyphenyl)methyl[4-[α-(1-methyl-2-phenylindol-3-yl)benzylidene]-2,5-cyclohexadien-1-ylidene]ammonium chloride Ammonium, [4-[α-2,1,3-benzothiadiazol-4-yl-p-(dimethylamino)benzylidene]-2,5-cyclohexadien-1-ylidene]dimethyl-, perchlorate Ammonium, [4-[p-(dimethylamino)-α-(5-methoxy-2,1,3-benzothiadiazol-4-yl)benzylidene]-2,5-cyclohexadien-1-ylidene]dimethyl-, perchlorate Ammonium, [4-[p-(dimethylamino)-α-(5-methoxy-2,1,3-benzothiadiazol-4-yl)benzylidene]-2,5-cyclohexadien-1-ylidene]diethyl-, perchlorate Ammonium, [4-[p-(diethylamino)-α-(7-methoxy-2,1,3-benzothiadiazol-4-yl)benzylidene]-2,5-cyclohexadien-1-ylidene]diethyl-, perchlorate Ammonium, [4-[p-(diethylamino)-α-(7-methoxy-2,1,3-benzothiadiazol-4-yl)benzylidene]-2,5-cyclohexadien-1-ylidene)dimethyl-, perchlorate Ammonium, (4-(p-(diethylamino)-α-(7-methyl-2,1,3-benzothiadiazol-4-yl)benzylidene)-2,5-cyclohexadien-1-ylidene]diethyl-, perchlorate Ammonium, [4-[p-(dimethylamino)-α-(7-methyl-2,1,3-benzothiadiazol-4-yl)benzylidene]-2,5-cyclohexadien-1-ylidene]dimethyl-, perchlorate Ammonium, [4-[α-2,1,3 benzothiadiazol-4-yl-p(diethylamino)benzylidene]-2,5-cyclohexadien-1-ylidene]diethyl-, perchlorate Ammonium, [4-[α-2,1,3-benzothiadiazol-5-yl-p(diethylamino)benzylidene]-2,5-cyclohexadien-1-ylidene]diethyl-, perchlorate Ammonium, [4-[α-2,1,3 benzothiadiazol-5-yl-p(diethylamino)benzylidene]-2,5-cyclohexadien-1-ylidene]dimethyl-, perchlorate Ammonium, methyl [4-[α-(1-methyl-2-phenylindol-3-yl)benzylidene]-2,5-cyclohexadien-1-ylidene]phenyl-, trichlorozincate(1-)

Methyl [4-[α-(1-methyl-2-phenylindol-3-yl)benzylidene)-2,5-cyclohexadien-1-ylidene)phenylammonium trichlorozincate Dimethyl [4-[α-(1-methyl-2-phenylindol-3-yl)benzylidene]-2,5-cyclohexadien-1-ylidene]-ammonium trichlorozincate Dimethyl [4-[α-(1-methyl-2-phenylindol-3-yl)benzylidene]-2,5-cyclohexadien-1-ylidene]ammonium trichlorozincate Indole, 3-[α-(4-imino-2,5-cyclohexadien-1-ylidene)benzyl]-1,2-dimethyl-, monohydrochloride Indole, 3-[α-[4-[(p-ethoxyphenyl)imino]-2,5-cyclohexadien-1-ylidene]benzyl]-1-methyl-2-phenyl-, monohydrochloride Ammonium, [4-[α-[9-(2-cyanoethyl)carbazol-3-yl]-p-(dimethylamino)benzylidene]-2,5-cyclohexadien-1-ylidene]dimethyl- Ammonium, [4-[α-carbazol-3-yl-p-(dimethylamino)benzylidene]-2,5-cyclohexadien-1-ylidene]dimethyl- Ammonium, [4-[α-[9-(2-cyanoethyl)carbazol-3-yl]benzylidene]-2,5-cyclohexadien-1-ylidene]dimethyl- Ammonium, [4-(α-carbazol-3-ylbenzylidene)-2,5-cyclohexadien-1-ylidene]dimethyl- 2,5-cyclohexadien-1-one, 2,6-di-tert-butyl-4-(α-morpholinobenzylidene)-

2,5-cyclohexadien-1-one, 2,6-di-tert-butyl-4-[α-(2,2-dimethyl-1-aziridinyl)benzylidene]-

2,5-cyclohexadien-1-one,4-(α-1-aziridinylbenzylidene)-2,6-di-tert-butyl- 2,5-cyclohexadien-1-one, 2,6-bis(1,1-dimethylethyl)-4-(phenyl-1-piperidinylmethylene)-

2,5-cyclohexadien-1-one, 2,6-di-tert-butyl-4-(α-piperidinobenzylidene)-

Ammonium, [4-[α-4-(diethylamino)-o-tolyl]piperonyl]-3-methyl-2,5-cyclohexadien-1-ylidene]diethyl-, chloride Ammonium, [4-[α-4-(diethylamino)-o-tolyl]-2-thenylidene]-3-methyl-2,5-cyclohexadien-1-ylidene]diethyl-, chloride Ammonium, [4-[α-[p-(diethylamino)phenyl]-5-nitrofurfurylidene]-2,5-cyclohexadien-1-ylidene]dimethyl-, chloride Ammonium, [4-[5-bromo-α-[p-diethylamino)phenyl]furfurylidene]-2,5-cyclohexadien-1-ylidene]diethyl-, chloride Ammonium, [4-[α-[p-(dimethylamino)phenyl]-2-furfurylidene]-2,5-cyclohexadien-1-ylidene]diethyl-, chloride 2-hydroxy-5-[[4-[[4-[(4-hydroxy-3-sulfophenyl)amino]phenyl](1-methyl-2-phenyl-1H-indol-3-yl)methylene]-2,5-cyclohexadien-1-ylidene]amino]-, Ammonium, [4-[α-12H-benzo[α]phenoxazin-5-yl-p-(dimethylamino)benzylidene]-2,5-cyclohexadien-1-ylidene]dimethyl, chloride, compound with zinc chloride

[4-[α-12H-benzo[α]phenoxazin-5-yl-p-(dimethylamino)benzylidene]-2,5-cyclohexadien-1-ylidene]dimethylammonium chloride Benzenamine, N,2-dimethyl-4-[(2-methyl-1H-indol-3-yl)[3-methyl-4-(methylimino)-2,5-cyclohexadien-1-ylidene]methyl]-, monohydrochloride Indole, 2-methyl-3-[3-methyl-4-(methylamino)-α-[3-methyl-4-(methylimino)-2,5-cyclohexadien-1-ylidene]benzyl]-monohydrochloride Methanaminium, N-[4-[[4-(dimethylamino)phenyl]-2-furanylmethylene]-2,5-cyclohexadien-1-ylidene]-N-methyl-, chloride Ammonium, [4-[α-[p-dimethylamino)phenyl]furfurylidene]-2,5-cyclohexadien-1-ylidene]dimethyl-, chloride Benzenaminium, N-[4-[[2-(4-chlorophenyl)-4,6-dimethyl-1-(2-methylpropyl)-1H-indol-3-yl](2,4-disulfophenyl)methylene]-2,5-cyclohexadien-1-ylidene]-4-methoxy-N-methyl-, Ammonium, [4-[α-[2-(p-chlorophenyl)-1-isobutyl-4,6-dimethylindol-3-yl]-2,4-disulfobenzylidene]-2,5-cyclohexadien-1-ylidene](p-methoxyphenyl)methyl-, hydroxyde, 2-ethoxy-5-[[4-[[4-[(4-ethoxy-3-sulfophenyl)amino]phenyl](1-methyl-2-phenyl-1H-indol-3-yl)methylene]-2,5-cyclohexadien-1-ylidene]amino]

5-[(3-carboxy-5-methyl-4-oxo-2,5-cyclohexadien-1-ylidene)(4,5-dihydro-3-methyl-5-oxo-1-phenyl-1H-pyrazol-4-yl)methyl]-2-hydroxy-3-methyl- 5-[[4-[[2-(4-chlorophenyl)-4,6-dimethyl-1-(2-methylpropyl)-1H-indol-3-yl][4-[(4-ethoxy-3-sulfophenyl)amino]phenyl]methylene]-2,5-cyclohexadien-1-ylidene]amino]-2-ethoxy-, N-[α-[2-(p-chlorophenyl)-1-isobutyl-4,6-dimethylindol-3-yl]-α-[4-[(4-ethoxy-3-sulfophenyl)imino]-2,5-cyclohexadien-1-ylidene]-p-tolyl]-6-ethoxy-, 6-[(4-ethoxyphenyl)imino]-3-[(1-methyl-2-phenyl-1H-indol-3-yl)[4-[(2-sulfoethyl)amino]phenyl]methylene]-, 6-[(p-ethoxyphenyl)imino]-3-[α-(1-methyl-2-phenylindol-3-yl)-p-[(2-sulfoethyl)amino]benzylidene]-, Methanaminium, N-[4-[[4-(dimethylamino)phenyl]-3-thienylmethylene]-2,5-cyclohexadien-1-ylidene]-N-methyl-, perchlorate

[4-[α-[p-(Dimethylamino)phenyl]-3-thenylidene]-2,5-cyclohexadien-1-ylidene]dimethylammonium perchlorate Ammonium, 4-[α-[p-(dimethylamino)phenyl]furfurylidene]-2,5-cyclohexadien-1-ylidene]dimethyl-, bromide

[4-[α-[p-(Dimethylamino)phenyl]furfurylidene]-2,5-cyclohexadien-1-ylidene]dimethylammonium bromide Methanaminium, N-[4-[[4-(dimethylamino)phenyl]-3-pyridinylmethylene]-2,5-cyclohexadien-1-ylidene]-N-methyl-, perchlorate Ammonium, [4-[p-(dimethylamino)-α-3-pyridylbenzylidene]-2,5-cyclohexadien-1-ylidene]dimethyl-, perchlorate

[4-[p-(Dimethylamino)-α-3-pyridylbenzylidene]-2,5-cyclohexadien-1-ylidene]dimethylammonium perchlorate Ammonium, [4-[p-(dimethylamino)-α-4-pyridylbenzylidene]-2,5-cyclohexadien-1-ylidene]dimethyl-, perchlorate

[4-[p-(Dimethylamino)-α-4-pyridylbenzylidene]-2,5-cyclohexadien-1-ylidene]dimethylammonium perchlorate Ammonium, [4-[p-(dimethylamino)-α-2-pyridylbenzylidene]-2,5-cyclohexadien-1-ylidene]dimethyl-, chloride and

[4-[p-(Dimethylamino)-α-2-pyridylbenzylidene]-2,5-cyclohexadien-1-ylidene]dimethylammonium chloride.

The monoheteroyldiarylmethanes of formulae (I) or (Ibis) and leuco compounds of formulae (II) or (IIbis) are known compounds. These compounds may be prepared according to synthesis processes well known in the literature and as described, for example, in Document Nos. DE-A-1 509 750, GB-A-1 139 407, GB-A-1 188 605, U.S. Pat. No. 3,652,556 and U.S. Pat. No. 3,685,956, GB-822 846, DE-1 254 118, GB-1 047 796, U.S. Pat. No. 3,423,427, DE-1 569 749, BE-702 839, BE-A-702 240, U.S. Pat. No. 3,995,088, U.S. Pat. No. 4,054,718, DE-2 917 271, U.S. Pat. No. 4,340,540, GB-A-2 075 539, U.S. Pat. No. 4,460,385, U.S. Pat. No. 5,094,688 and U.S. Pat. No. 5,097,034.

It is found that, surprisingly, at least some of the compositions disclosed herein can be used to obtain intense colorations, even on non-sensitized hair.

With at least one of the compositions disclosed herein, a variety of chromatic or dark, very bright, only slightly selective and durable glints may be obtained.

Thus, when the at least one dye of formulae (I), (Ibis), (II) and (IIbis) is included in the compositions disclosed herein any shade from green to blue, passing through red may be obtained and, for example, black shades may also be obtained.

The colorations obtained with the compositions disclosed herein may have at least one of the following advantages: durable, stable, resistant to bad weather, washing, sweat, friction and subsequent treatments such as permanent wavings.

For example, these colorations may be resistant to light.

The at least one dye may be present in an amount ranging from approximately 0.0001% to approximately 10% by weight, for example, from approximately 0.005% to approximately 10% by weight and, even further, for example, from approximately 0.01% to approximately 6% by weight, relative to the total weight of the dye composition.

The dye compositions disclosed herein may further comprise at least one additional direct dye different from the at least one dye chosen from formulae (I), (Ibis), (II) and (IIbis). The at least one additional direct dye may, for example, be chosen from neutral, acid and cationic benzenic nitrated direct dyes; neutral, acid and cationic azoic direct dyes; quinonic direct dyes, such as, neutral, acid and cationic anthraquinonic direct dyes; azinic direct dyes; triarylmethanic direct dyes; indoaminic direct dyes; and natural direct dyes.

Non-limiting examples of benzenic direct dyes include the following dyes:

1,4-diamino-2-nitrobenzene;
1-amino-2-nitro-4-β-hydroxyethylaminobenzene;
1-amino-2-nitro-4-bis(β-hydroxyethyl)aminobenzene;
1,4-Bis(β-hydroxyethylamino)-2-nitrobenzene;
1-β-hydroxyethylamino-2-nitro-4-bis-(β-hydroxyethylamino)-benzene;
1-β-hydroxyethylamino-2-nitro-4-aminobenzene;
1-β-hydroxyethylamino-2-nitro-4-(ethyl)(β-hydroxyethyl)-aminobenzene;
1-amino-3-methyl-4-β-hydroxyethylamino-6-nitrobenzene;
1-amino-2-nitro-4-β-hydroxyethylamino-5-chlorobenzene;
1,2-Diamino-4-nitrobenzene;
1-amino-2-β-hydroxyethylamino-5-nitrobenzene;
1,2-Bis-(β-hydroxyethylamino)4-nitrobenzene;
1-amino-2-tris-(hydroxymethyl)-methylamino-5-nitrobenzene;
1-Hydroxy-2-amino-5-nitrobenzene;
1-Hydroxy-2-amino-4-nitrobenzene;
1-Hydroxy-3-nitro-4-aminobenzene;
1-Hydroxy-2-amino-4,6-dinitrobenzene;
1-β-hydroxyethyloxy-2-β-hydroxyethylamino-5-nitrobenzene;
1-Methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis-(β-hydroxyethyl)-amino-3-nitrobenzene;
1-β-hydroxyethylamino-2-nitrobenzene; and
1-Hydroxy-4-β-hydroxyethylamino-3-nitrobenzene.

The azoic direct dyes may, for example, be chosen from the cationic azoic dyes described in Patent Application Nos. WO-A-95/15144, WO-A-95/01772, EP-A-714954 and WO-A-01/66646, the disclosure of which related to such azoic direct dyes are specifically incorporated herein by reference.

For example, the azoic direct dyes may be chosen from one or more of:

1,3-dimethyl-2-[[4-(dimethylamino)phenyl]azo]-1H-Imidazolium chloride;
1,3-dimethyl-2-[(4-(aminophenyl)azo]-1H-Imidazolium chloride; and
1-methyl-4-[(methylphenylhydrazono)methyl]-pyridinium methylsulfate.

The azoic direct dyes may also be chosen, for example, from one or more of the following dyes described in the COLOUR INDEX INTERNATIONAL 3rd EDITION:

Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

1-(4'-aminodiphenylazo)-2-methyl-4bis-(β-hydroxyethyl)aminobenzene and 4-hydroxy-3-(2-methoxyphenylazo)-1-naphthalene sulphonic acid may also be used in the compositions disclosed herein.

The quinonic direct dyes may, for example, be chosen from one or more of the following dyes:

Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99, and also the following compounds:

1-N-methylmorpholiniumpropylamino-4-hydroxyanthraquinone;
1-Aminopropylamino-4-methylaminoanthraquinone;
1-Aminopropylaminoanthraquinone;
5-β-hydroxyethyl-1,4-diaminoanthraquinone;
2-Aminoethylaminoanthraquinone;
1,4-Bis-(β-γ-dihydroxypropylamino)-anthraquinone.

The azinic dyes may, for example, be chosen from one or more of the following dyes:

Basic Blue 17; and
Basic Red 2.

The triarylmethanic dyes may, for example, be chosen from one or more of the following dyes:

Basic Green 1;
Acid Blue 9;
Basic Violet 3;
Basic Violet 14;
Basic Blue 7;
Acid Violet 49;
Basic Blue 26; and
Acid Blue 7.

The indoaminic dyes may, for example, be chosen from one or more of the following:

2-β-hydroxyethylamino-5-[bis-(β-4'-hydroxyethyl)amino]anilino-1,4-benzoquinone;
2-β-hydroxyethylamino-5-[2'-methoxy-4'-amino)anilino-1,4-benzoquinone;
3-N(2'-Chloro-4'-hydroxy)phenyl-acetylamino-6-methoxy-1,4-benzoquinone imine;
3-N(3'-Chloro-4'-methylamino)phenyl-ureido-6-methyl-1,4-benzoquinone imine; and
3-N[4'-N-(Ethyl, carbamylmethyl)amino]-phenyl-ureido-6-methyl-1,4-benzoquinone imine.

The natural direct dyes that may be used in the compositions disclosed herein may be chosen, for example, from one or more of lawsone, juglone, alizarine, purpurine, carminic acid, kermesic acid, purpurogalline, protocatechaldehyde, indigo, isatine, curcumine, spinulosine and apigenidine. Extracts or decoctions comprising these natural dyes, for example, cataplasms or henna based extracts can also be used.

The at least one additional direct dye may be present, for example, in an amount ranging from approximately 0.001% to approximately 20% by weight, and further, for example, from approximately 0.005% to approximately 10% by weight, relative to the total weight of the composition.

The compositions disclosed herein may further comprise at least one oxidation base and optionally at least one coupler. The at least one oxidation base and the at least one coupler may each be chosen from those conventionally used for oxidation dyeing.

For example, the at least one oxidation base may be chosen from paraphenylenediamines, bis-phenylalkylenediamines, para-aminophenols, ortho-aminophenols, heterocyclic bases and the addition salts thereof.

For example, the at least one coupler may be chosen from metaphenylenediamine couplers, meta-aminophenol couplers, metadiphenol couplers, naphthalenic couplers, heterocyclic couplers and the addition salts thereof.

When the at least one oxidation base and the optionally least one coupler are present in the compositions disclosed herein, they each may be present in an amount ranging, for example, from approximately 0.001% to approximately 10% by weight, and, further, for example, from approximately 0.005% to approximately 6% by weight, relative to the total weight of the dye composition.

The medium suitable for dyeing, also called the dye support, may, for example, be chosen from water and a mixture of water and at least one organic solvent to solubilize compounds that would not be sufficiently water-soluble. For example, the at least one organic solvent may be chosen from $C_1$–$C_4$ lower alkanols, such as ethanol and isopropanol; polyols and polyol ethers such as 2-butoxyethanol, propyleneglycol, propyleneglycol monomethylether, diethyleneglycol monoethylether and monomethylether; and aromatic alcohols such as benzylic alcohol and phenoxyethanol.

The solvents may be present in an amount ranging, for example, from approximately 1% to approximately 40% by weight, and even further, for example, from approximately 5% to approximately 30% by weight.

The dye compositions disclosed herein may further comprise at least one additive chosen from those conventionally used in compositions for dyeing the hair, such as anionic, cationic, non-ionic, amphoteric, and zwitterionic surfactants; anionic, cationic, non-ionic, amphoteric, and zwitterionic polymers; mineral and organic thickeners, and, for example, anionic, cationic, non-ionic and amphoteric polymer associative thickeners; antioxidants; penetration agents; sequestering agents; fragrances (perfumes); buffers; dispersants; conditioning agents such as modified and non-modified volatile and non-volatile silicones; film-forming agents; ceramides; preservatives; and opacifying agents.

The at least one additive may each be present, for example, in an amount ranging from approximately 0.01% to approximately 20% by weight, relative to the total weight of the composition.

For example, the compositions disclosed herein may comprise at least one organic solvent chosen from $C_2$–$C_4$ alkanols and polyols with a molecular weight of less than 1000.

For example, the compositions disclosed herein may comprise at least one additive chosen from surfactants and mineral and organic thickeners.

Obviously, one skilled in the art will take care to chose this or these additional additive(s) so that at least one advantageous property intrinsically attached to the dye compositions disclosed herein are not modified or are not substantially modified by the envisaged addition(s).

The pH of the dye compositions disclosed herein may range, for example, from about 3 to about 12, further, for example, from about 5 to about 11, and even further, for example, from about 6 to about 8.5.

It may be adjusted to the required value by means of at least one agent chosen from acidifying agents and alkalizing agents usually used for dyeing keratin fibers or by using conventional buffer systems.

The acidifying agents may, for example, be chosen from mineral and organic acids like hydrochloric acid, orthophosphoric acid, and sulphuric acid, and carboxylic acids like acetic acid, tartric acid, citric acid, lactic acid, and sulfonic acids.

The alkalizing agents may, for example, be chosen from ammonia, alkaline carbonates, alkanolamines such as mono-, di- and triethanolamines and derivatives thereof, sodium and potassium hydroxides and compounds with the formula (III) given below:

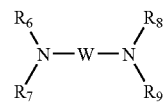

(III)

wherein:

W is a propylene moiety optionally substituted with at least one entity chosen from hydroxyl and $C_1$–$C_4$ alkyls; $R_6$, $R_7$, $R_8$ and $R_9$, which may be identical or different, are each chosen from hydrogen, $C_1$–$C_4$ alkyl, and $C_1$–$C_4$ hydroxyalkyl.

The dye compositions disclosed herein may be provided in various forms, such as in a form chosen from liquids, creams, gels and any other suitable forms to achieve dyeing of keratin fibers, such as human hair.

Further disclosed herein is a method for the direct dyeing of keratin fibers, for example, human keratin fibers such as hair, comprising applying at least one dye composition comprising at least one dye of formula (I), (Ibis), (II) or (IIbis) as defined above on keratin fibers. After observing a pause time, the keratin fibers may be rinsed allowing coloured fibers to appear. The pause time may range, for example, from about 3 minutes to about 50 minutes, and further, for example, from about 5 minutes to about 30 minutes.

As used herein, "direct colouring" or "dyeing (tinting)" means dyeing without an oxidant other than the oxygen in the air.

When the at least one dye composition comprises at least one dye chosen either from formulae (II) and (IIbis) as defined herein or from formulae (I) and (Ibis) as defined herein and at least one oxidation base, and optionally at least one coupler, the at least one dye composition may, for example, comprise at least one oxidizing agent.

Therefore, further disclosed herein is a method for dyeing keratin fibers, for example, human keratin fibers such as, hair, comprising applying least one dye composition, in a cosmetic medium suitable for dyeing, at least one oxidation base and optionally at least one coupler and at least one dye chosen from either formulae (II) and (IIbis), or from formulae (I) and (Ibis) and, developing the color at an acid, neutral or alkaline pH by applying to the keratin fibers at least one oxidizing agent.

The at least one oxidizing agent may, for example, be chosen from hydrogen peroxide, urea peroxide, alkaline metal bromates, persalts such as perborates and persulfates, peracids and oxidase enzymes, such as peroxidases, oxydoreductases with two electrons such as uricases and oxygenases with four electrons such as laccases. Hydrogen peroxide may, for example, be used in the compositions disclosed herein.

The at least one oxidizing agent may be added to the compositions disclosed herein just at the time of use or it may be added starting from at least one oxidizing composition comprising it, applied simultaneously to or sequentially with the at least one dye composition disclosed herein.

The at least one oxidizing composition may further comprise at least additive chosen from those conventionally used in compositions for dyeing hair and as defined above.

If the at least one oxidizing composition is mixed with the at least one dye composition, the pH of the at least one oxidizing composition comprising the at least one oxidizing agent is such that after mixing with the at least one dye composition, the pH of the resulting composition applied on the keratin fibers ranges, for example, from about 3 to about 12, and, further, for example, from about 5 to about 11, and even further, for example, from about 6 to about 8.5. The pH may be adjusted to the desired value by means of at least one agent chosen from acidifying agents and alkalizing agents usually used in the dyeing of keratin fibers and as defined above.

The composition that is finally applied on the keratin fibers may be in various forms, such as in a form chosen from liquids, creams and gels and any other appropriate forms for dyeing keratin fibers, such as human hair.

Further disclosed herein is a multicompartment device or "kit" comprising at least one compartment comprising at least one dye composition as defined above, comprising at least one dye chosen from either formulae (II) and (IIbis) as defined herein, or from formulae (I) and (Ibis) as defined herein and at least one oxidation base and optionally at least one coupler, and at least one additional compartment comprising at least one oxidizing composition.

This device may be equipped with a means of delivering the desired mixture on the hair, such as devices described in Patent No. FR-2 586 913.

In the case of a composition comprising at least one dye chosen from formulae (II) and (IIbis), it is desirable to avoid contact between the at least one dye and oxygen in the air. An aerosol device can, for example, be the suitable packaging mode.

With the dyes disclosed herein, direct lightening dyeing is also possible in the absence of oxidation dyes and in the presence of at least one oxidizing agent in such conditions (for example hydrogen peroxide in an alkaline medium) so that the at least one oxidizing agent could make the keratin fibers lighter by action on pigments initially present in said fibers.

The following examples illustrate the various embodiments disclosed herein without, however, being limiting in nature.

EXAMPLE 1

The following dye composition was prepared:

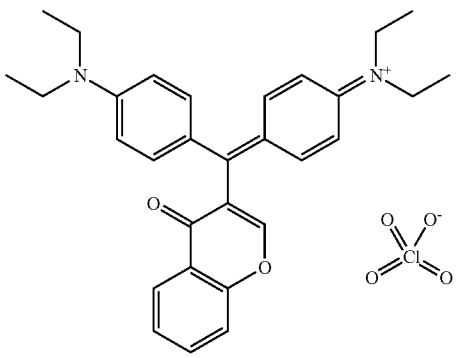

| | |
|---|---|
| Ethanaminium, N-[4-[[4-(diethylamino)phenyl](4-oxo-4H-1-benzopyran-3-yl)methylene]-2,5-cyclohexadien-1-ylidene]-N-ethyl-, perchlorate | 0.553 g |
| Oleic diethanolamide | 3 g |
| Lauric acid | 1 g |
| Ethyleneglycol monoethylether | 5 g |
| Hydroxyethylcellulose | 2 g |
| 2-amino-2-methyl-1-propanol | q.s . . . pH 9.5 |
| Deionised water | q.s. 100 g |

The above composition was applied to locks of natural grey hair or permed hair containing 90% white hair and was allowed to stand for 30 minutes. After rinsing with running water and drying, the hair was tinted in a green shade.

EXAMPLE 2

The following dye composition was prepared for obtaining a black grey shade with violet glints:

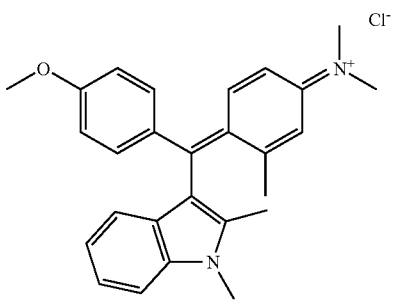

| | |
|---|---|
| {4-[(1,2-Dimethyl-1H-indol-3-yl)-(4-methoxy-phenyl)-methylene]-cyclohexa-2,5-dienylidene}-dimethylammonium chloride | 0.569 g |
| Benzylic alcohol | 4.0 g |
| Polyethyleneglycol 60E | 6.0 g |
| Hydroxyethylcellulose | 0.7 g |
| Alkylpolyglucoside in aqueous solution at 60% A.M.* | 4.5 g A.M. |
| Phosphate buffer | q.s pH 7 |
| Deionised water | q.s. 100.00 g |

* Active Material

EXAMPLES 3 TO 5

The three direct dye compositions defined in the following table were prepared:

(all contents are expressed in grams)

| Example 3 | Example 4 | Example 5 |
|---|---|---|
| Methanaminium,N [4[[4-(dimethylamino) phenyl)-2-thienylmethylene]-2,5-cyclohexadien-1-ylidene]-N-methyl chloride | {4-[(4-Dymethylamino-phenyl)-(1-ethyl-2-methyl-3a,7a-dihydro-1H-indol-3-yl)-methylene] cyclohexa-2,5-dienylidene]dimethylammonium trichloro-zincate | [4-[p-Dimethyl amino)-α-(9-methylcarbazol-3-yl)benzylidene]-2,5-cyclohexadien-1-ylidene]dimethyl ammonium Chloride |

|  | Example 3 | Example 4 | Example 5 |
|---|---|---|---|
| Direct dye formula (3) | 0.2 | | |
| Direct dye formula (4) | | 0.2 | |
| Direct dye formula (5) | | | 0.2 |
| Cross-linked polyacrylic acid sold by the Goodrich company under the name Carbopol 2984 | 1.0 A.M.* | | |
| Ammonium acrylate/acrylamide copolymer sold by the Hoechst company under the name Bozepol C Nouveau (New) | | 1.0 A.M.* | |
| Cross-linked methacrylic acid/ethyl acrylate copolymer sold in aqueous dispersion with 38% active material by the Coatex company under the name Viscoatex 538C | | | 1.0 A.M.* |
| Cross-linked acrylic acid/ ethyl acrylate copolymer sold in aqueous dispersion with 28% active material by the Rohm & Haas Company under the name Aculyn 33 | | | |
| Ethanol | 10 | 10 | 10 |
| 2-amino-2-methyl-1-propanol . . . qs | pH 9 | pH 9 | pH 9 |
| Deionised water . . . qs | 100 | 100 | 100 |

A.M.*denotes Active Material

The above compositions were applied for 30 minutes each on locks of natural greyhair with 90% white hair. The locks of hair were then rinsed, washed with a standard shampoo and then dried.

The locks were dyed in the following shades:

| Examples | Shade obtained |
|---|---|
| 3 | Bright green |
| 4 | Bright violet |
| 5 | Bright blue |

EXAMPLES 6 TO 9

Compositions 6 (A) to 9 (A) according to the present disclosure were prepared, as follows (contents in grams):

| COMPOSITION | 6 (A) | 7 (A) | 8 (A) | 9 (A) |
|---|---|---|---|---|
| Paratoluylenediamine | 0.25 | — | — | — |
| Para-aminophenol | 0.30 | 0.50 | 0.15 | — |
| Paraphenylenediamine | — | 0.20 | — | 0.30 |
| 5-N-(β-hydroxyethyl)amino 2-methyl phenol | 0.5 | 0.8 | 0.17 | — |
| 5-amino 2-methyl phenol | — | — | — | 0.30 |
| Dye having the formula (3) | 0.15 | — | — | — |
| Dye having the formula (4) | — | 0.20 | 0.05 | — |
| Dye having the formula (5) | — | — | — | 0.1 |
| Common dye support (*) | (*) | (*) | (*) | (*) |
| Water q.s. | 100 g | 100 g | 100 g | 100 g |

| (*) common dye support: | |
|---|---|
| Polyglycerolated oleic acid with 2 moles of glycerol | 4.0 g |
| Polyglycerolated oleic acid with 4 moles of glycerol, and 78% of active materials (A.M.) | 5.69 g A.M. |
| Oleic acid | 3.0 g |
| Oleic amine with 2 moles of ethylene oxide sold under the commercial name ETHOMEEN 012 by the AKZO company | 7.0 g |
| Diethylaminopropyl laurylaminosuccinamate, sodium salt with 55% A.M. | 3.0 g A.M. |

-continued

| COMPOSITION | 6 (A) | 7 (A) | 8 (A) | 9 (A) |
|---|---|---|---|---|
| Oleic alcohol | | | 5.0 g | |
| Oleic acid diethanolamide | | | 12.0 g | |
| Prolyleneglycol | | | 3.5 g | |
| Ethyl alcohol | | | 7.0 g | |
| Dipropyleneglycol | | | 0.5 g | |
| Prolyleneglycol monomethylether | | | 9.0 g | |
| Sodium metabisulfite in aqueous solution, with 35% A.M. | | | 0.455 g A.M | |
| Ammonium acetate | | | 0.8 g | |
| Anti-oxidant, sequestering agent | | | q.s. | |
| Flagrance, preservative | | | q.s. | |
| Ammonia with 20% $NH_3$ | | | 10.0 g | |

At the time of use, each of these compositions 6 (A) to 9 (A) was mixed with an equal quantity of a composition (B) comprising a solution of hydrogen peroxide 20 volumes (6% by weight).

Each resulting composition (ready-to-use composition according to the present disclosure) was applied for 30 minutes to locks of natural grey hair with 90% white. The hair locks were then rinsed, washed with a standard shampoo and then dried.

The hair strands were dyed in the shades shown in the following table:

| EXAMPLE [COMPOSITION] | SHADE OBTAINED |
|---|---|
| 6 [6 (A)] | Dark blond with green glints |
| 7 [7 (A)] | Blond with intense violet glints |
| 8 [8 (A)] | Light blond with violet glints |
| 9 [9 (A)] | Blond with blue glints |

The shades obtained had a very good resistance to subsequent shampooings.

According to one variant of the present disclosure, the direct dyes may be incorporated in the dyeing compositions at the time of use.

EXAMPLE 10

The following composition 10 (A) was prepared:

| | |
|---|---|
| 1,4-diamino benzene | 0.40 g |
| 5-amino 2-methyl phenol | 0.45 g |
| Common dye support as described previously for examples 1 to 4 (*) | |
| deionized water q.s. | 100 g |

The following composition 10 (A') was prepared:

| | |
|---|---|
| Dye of example 4 | 4 g |
| Quaternary polyammonium sold by the National Starch Company under the commercial name CELQUAT SC-240 | 10 g |
| Wood sawdust q.s. | 100 g |

At the time of use, one part by weight of composition 10 (A) above was mixed with 0.1 part by weight of composition 10 (A') and with one part by weight of a composition (B) comprising a solution of 20 volumes hydrogen peroxide (6% by weight).

The resulting composition was applied onto locks of natural grey hair with 90% white, for 30 minutes. The hair was then rinsed and washed with a standard shampoo and then dried.

The hair was dyed in a light auburn shade with intense violet glints, that resisted to subsequent washings very well.

What is claimed is:

1. A composition for dyeing keratin fibers comprising:
   a cosmetic medium suitable for dyeing human keratin fibers, wherein said medium is water or a mixture of water and at least one organic solvent suitable for dyeing human keratin fibers, and
   at least one dye, comprised in said medium and chosen from formulae (I), (Ibis), (II) and (IIbis) and the tautomeric forms thereof and the addition salts thereof:

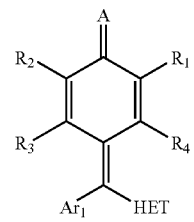

(I)

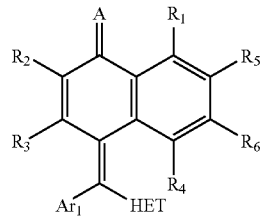

(Ibis)

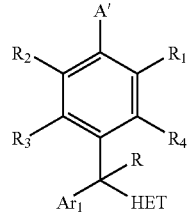

(II)

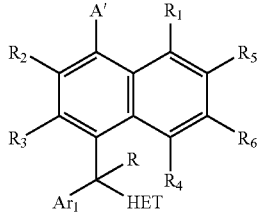

(IIbis)

wherein:
   $Ar_1$, which may be identical or different, is chosen from aryl optionally substituted with at least one Z group;
   HET, which may be identical or different, is chosen from heterocycles optionally substituted with at least one Z' group;
   A, which may be identical or different, is chosen from O; NH; N-alkyl; N-hydroxyalkyl; ammonium, N-alkylammonium, N-(hydroxyalkyl)ammonium, N,N-dialkylammonium, N,N-di(hydroxyalkyl)ammonium, and N-(hydroxyalkyl) N-(alkyl)ammonium wherein the two alkyl groups may form, together with the nitrogen atom to which they are bonded, at least one cyclic group optionally interrupted by at least one atom chosen from nitrogen, oxygen and sulphur;

$R_1$ to $R_6$, Z, and Z', which may be identical or different, are each chosen from hydrogen, halogen, —NHSO$_3$H; hydroxyl; alkyl; alkoxy; alkylthio; monoalkylamino, and dialkylamino, wherein the two alkyl groups of the dialkylamino may form together with the nitrogen atom to which they are bonded, at least one cyclic group optionally interrupted by at least one atom chosen from nitrogen, oxygen and sulphur; heterocycles and nitro; aryl; acyl; alkoxycarbonyl; carboxamido; cyano; —CO$_2$H; —SO$_3$H; —PO$_3$H$_2$; and —PO$_4$H$_2$;

A', which may be identical or different, is chosen from hydrogen; hydroxyl; amino; (hydroxyalkyl)amino; monoalkylamino; (dihydroxyalkyl)amino, (hydroxyalkyl)(alkyl)amino, (dialkyl)amino, wherein the two alkyl groups of the (dialkyl)amino may form, together with the nitrogen atom to which they are bonded, at least one cyclic group optionally interrupted by at least one atom chosen from nitrogen, oxygen and sulphur; and R is chosen from hydrogen, halogens, hydroxyl, alkoxy, and alkylthio.

2. The composition according to claim 1, wherein the keratin fibers are hair.

3. The composition according to claim 1, wherein the aryl, of $Ar_1$, is chosen from phenyl and naphthyl.

4. The composition according to claim 1, wherein the halogen, of $R_1$ to $R_6$, Z, and Z', is chosen from F, Cl, Br and I.

5. The composition according to claim 1, wherein HET is chosen from unsaturated heterocycles, optionally substituted by at least one Z' group.

6. The composition according to claim 5, wherein HET is chosen from aromatic heterocycles optionally substituted with at least one Z' group.

7. The composition according to claim 1, wherein the heterocycles are chosen from thiophene, benzothiophene, furan, benzofuran, indole, indoline, carbazole, pyridine, dehydroquinoleine, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

8. The composition according to claim 7, wherein HET is chosen from thiophene, benzothiophene, furan, benzofuran, indole, indoline, carbazole, pyridine, dehydroquinoleine, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

9. A composition for dyeing keratin fibers comprising:
a cosmetic medium suitable for dyeing human keratin fibers, wherein said medium is water or a mixture of water and at least one organic solvent suitable for dyeing human keratin fibers, and
at least one dye, comprised in said medium and chosen from the following compounds, for which the counter ions are specified or not specified, and the tautomeric forms thereof and the addition salts thereof chosen from:

Methanaminium, N-[4-[[4-(dimethylamino)phenyl](2,2-dimethyl-2H-1-benzopyran-3-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-3-yl)methylene]-2,5-cyclohexadien-1-ylidene]-N-methyl, Methanaminium, N-[4-[[4-(dimethylamino)phenyl](2,2-dimethyl-2H-1-benzopyran-5-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-5-yl)methylene]-2,5-cyclohexadien-1-ylidene]-N-methyl-, Methanaminium, N-[4-[[4-(dimethylamino)phenyl](2,2-dimethyl-2H-1-benzopyran-4-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-4-yl)methylene]-2,5-cyclohexadien-1-ylidene]-N-methyl-, Methanaminium, N-[4-[[4-(dimethylamino)phenyl](2,2-dimethyl-2H-1-benzopyran-8-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-8-yl)methylene]-2,5-cyclohexadien-1-ylidene]-N-methyl-, Methanaminium, N-[4-[[4-(dimethylamino)phenyl](2,2-dimethyl-2H-1-benzopyran-7-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-7-yl)methylene]-2,5-cyclohexadien-1-ylidene]-N-methyl-, Methanaminium, N-[4-[[4-(dimethylamino)phenyl](2,2-dimethyl-2H-1-benzopyran-6-yl)methylene]-2,5-cyclohexadien-1-ylidene]-N-methyl-, acetate, Methanaminium, N-[4-[[4-(dimethylamino)phenyl](2,2-dimethyl-2H-1-benzopyran-6-yl)methylene]-2,5-cyclohexadien-1-ylidene]-N-methyl-, 2,5-Cyclohexadien-1-one, 4-[[4-amino-3,5-bis(1-methylethyl)phenyl](4-ethyl-3,4-dihydro-2H-1,4-benzoxazin-7-yl)methylene]-2,6-dimethoxy, 2,5-Cyclohexadien-1-one, 4-[[3,4-dihydro-4-(2-pyridinylmethyl)-2H-1,4-benzoxazin-7-yl](4-ethyl-3,4-dihydro-2H-1,4-benzoxazin-7-yl)methylene]-2,6-dimethoxy-, 2,5-Cyclohexadien-1-one, 4-[[4-(dimethylamino)phenyl](4-ethyl-3,4-dihydro-2H-1,4-benzoxazin-7-yl)methylene]-2,6-dimethoxy- 2,5-Cyclohexadien-1-one, 2,6-bis(1,1-dimethylethyl)-4-[(5-ethyl-2-thienyl)phenylmethylene]-, Ethanaminium, N-[3-carboxy-4-[[2-carboxy-4-[ethyl(2-methoxyethyl)amino]phenyl](7-carboxy-4-oxo-4H-1-benzothiopyran-3-yl)methylene]-2,5-cyclohexadien-1-ylidene]-N-ethyl-2-methoxy, Ethanaminium, N-[4-[[4-[bis(2-methoxyethyl)amino]-2-carboxyphenyl](5-carboxy-2-pyridinyl)methylene]-3-carboxy-2,5-cyclohexadien-1-ylidene]-2-methoxy-N-(2-methoxyethyl)-, Ethanaminium, N-[4-[3-benzofuranyl[2-carboxy-4-[ethyl[2-(methylsulfonyl)amino]ethyl]amino]phenyl]methylene]-3-carboxy-2,5-cyclohexadien-1-ylidene]-N-ethyl-2-[(methylsulfonyl)amino]-, perchlorate, Ethanaminium, N-[4-[3-benzofuranyl[2-carboxy-4-[ethyl[2-[(methylsulfonyl)amino]ethyl]amino]phenyl]methylene]-3-carboxy-2,5-cyclohexadien-1-ylidene]-N-ethyl-2-[(methylsulfonyl)amino]-, Ethanaminium, N-[4-[[4-[bis(2-methoxyethyl)amino]-2-carboxyphenyl](4-oxo-4H-1-benzothiopyran-3-yl)methylene]-3-carboxy-2,5-cyclohexadien-1-ylidene]-2-methoxy-N-(2-methoxyethyl)-acetate, Ethanaminium, N-[4-[[4-[bis(2-methoxyethyl)amino]-2-carboxyphenyl](4-oxo-4H-1-benzothiopyran-3-yl)methylene]-3-carboxy-2,5-cyclohexadien-1-ylidene]-2-methoxy-N-(2-methoxyethyl)-, Benzoic acid and, 5-[(3-carboxy-4-oxo-2,5-cyclohexadien-1-ylidene)-3-pyridinylmethyl]-2-hydroxy-salt, Methanaminium, N-[2-carboxy-4-[[3-carboxy-4-(dimethylamino)phenyl](4-oxo-4H-1-benzothiopyran-3-yl)methylene]-2,5-cyclohexadien-1-ylidene]-N-methyl-, perchlorate, Methanaminium, N-[2-carboxy-4-[[3-carboxy-4-(dimethylamino)phenyl](4-oxo-4H-1-benzothiopyran-3-yl)methylene]-2,5-cyclohexadien-1-ylidene]-N-methyl-, Benzoic acid and 5-[(3-carboxy-4-oxo-2,5-cyclohexadien-1-ylidene)[3,5-dimethyl-1-[2-[(methylsulfonyl)amino]ethyl]-1H-pyrazol-4-yl]methyl]-2-hydroxy-salt, Benzoic acid and 5-[[2-[bis(2-methoxyethyl)amino]-5-thiazolyl](3-carboxy-4-oxo-2,5-cyclohexadien-1-ylidene)methyl]-2-hydroxy-salt, Ethanaminium, N-[4-[(7-carboxy-2-oxo-2H-1-benzopyran-4-yl)[4-(diethylamino)phenyl]methylene]-2,5-cyclohexadien-1-ylidene]-N-ethyl-, perchlorate, Ethanaminium, N-[4-[(7-carboxy-2-oxo-2H-1-benzopyran-4-yl)[4-(diethylamino)phenyl]methylene]-2,5-cyclohexadien-1-ylidene]-N-ethyl-, Ethanaminium, N-[4-[2-benzofuranyl[4-[ethyl[2-[(methylsulfonyl)amino]ethyl]amino]phenyl]methylene]-2,5-cyclohexadien-1-ylidene]-N-ethyl-2-[(methylsulfonyl)amino]-, perchlorate, Ethanaminium, N-[4-[2-benzofuranyl[4-[ethyl[2-[(methylsulfonyl)amino]ethyl]amino]phenyl]methylene]-2,5-cyclohexadien-1-ylidene]-N-ethyl-2-[(methylsulfonyl)amino]-, Ethanaminium, N-[4-[(6-carboxybenzo[b]thien-2-yl)[4-(diethylamino)phenyl]methylene]-2,5-cyclohexadien-1-ylidene]-N-ethyl-, tetrafluoroborate(1-), Ethanaminium, N-[4-[(6-carboxybenzo[b]thien-2-yl)[4-(diethylamino)phenyl]methylene]-2,5-cyclohexadien-1-ylidene]-N-ethyl-, Ethanaminium, N-[4-[[5-[bis(2-methoxyethyl)amino]-2-furanyl][4-[ethyl[2-(methylsulfonyl)amino]ethyl]amino]phenyl]methylene]-2,5-cyclohexadien-1-ylidene]-N-ethyl-2-[(methylsulfonyl)amino]-, perchlorate, Ethanaminium, N-[4-[[5-[bis(2-methoxyethyl)amino]-2-furanyl][4-[ethyl[2-[(methylsulfonyl)amino]ethyl]amino]phenyl]methylene]-2,5-cyclohexadien-1-ylidene]-N-ethyl-2-[(methylsulfonyl)amino]-, 2,5-Cyclohexadien-1-one, 4-[(4-hydroxyphenyl)-4-quinolinylmethylene]-, Ethanaminium, N-[4[[4-[Bis(2-methoxyethyl)amino]phenyl](7-carboxy-4-oxo-4H-1-benzopyran-3-yl)methylene]-2,5-cyclohexadien-1-ylidene]-2-methoxy-N-(2-methoxyethyl)-, sulfate (1:1), Ethanaminium, N-[4-[[4-[bis(2-methoxyethyl)amino]phenyl](7-carboxy-4-oxo-4H-1-benzopyran-3-yl)methylene]-2,5-(cyclohexadien-1-ylidene]-2-methoxy-N-(2-methoxyethyl)-, Methanaminium, N-[4-[(5-carboxy-2-pyridinyl)[4-(dimethylamino)phenyl]methylene]-2,5-cyclohexadien-1-ylidene]-N-methyl-, perchlorate, Methanaminium, N-[4-[(5-carboxy-2-pyridinyl)[4-(dimethylamino)phenyl]methylene]-2,5-cyclohexadien-1-ylidene]-N-methyl-, 2-Thiophenecarboxylic acid, 5-[(4-hydroxyphenyl)(4-oxo-2,5-cyclohexadien-1-ylidene)methyl]-

2,5-Cyclohexadien-1-one, 4-[2-furanyl(4-hydroxyphenyl)methylene]-, 2,5-Cyclohexadien-1-one, 4-[(4-hydroxyphenyl)-2-pyridinylmethylene]-, Methanaminium, N-[3-carboxy-4-[[2-carboxy-4-(dimethylamino)phenyl](4-oxo-4H-1-benzopyran-3-yl)methylene]-2,5-cyclohexadien-1-ylidene]-N-methyl, perchlorate, Methanaminium, N-[3-carboxy-4-[[2-carboxy-4-(dimethylamino)phenyl](4-oxo-4H-1-benzopyran-3-yl)methylene]-2,5-cyclohexadien-1-ylidene]-N-methyl-, Ethanaminium, N-[4-[(5-carboxy-2-thienyl)[4-(diethylamino)phenyl]methylene]-2,5-cyclohexadien-1-ylidene]-N-ethyl-, perchlorate, Ethanaminium, N-[4-[(5-carboxy-2-thienyl)[4-(diethylamino)phenyl]methylene]-2,5-cyclohexadien-1-ylidene]-N-ethyl-, 2,5-Cyclohexadien-1-one, 4-[(4-methoxyphenyl)-3,6,9,12,15-pentaoxabicyclo[15,3.1]heneicosa-1(21),17,19-trien-21-ylmethylene]-,-3,6,9,12,15-Pentaoxabicyclo[15,3,1]heneicosane,2,5-cyclohexadien-1-one, Methanaminium, N-[4-[(2,3-dihydro-3-methyl-2-benzothiazolyl)[4-(dimethylamino)phenyl]methylene]-2,5-cyclohexadien-1-ylidene]-N-methyl-, chloride,

[4-(α-Benzo[b]thien-2-yl-p-dimethylaminobenzylidene)-2,5-cyclohexadien-1-ylidene]dimethylammonium chloride,

[4-(α-Benzo[b]thien-3-yl-p-dimethylaminobenzylidene)-2,5-cyclohexadien-1-ylidene]dimethylammonium chloride, Methanaminium, N-[4-[[9-(dimethylamino)benzo[a]phenoxazin-7-ium-5-yl][4-dimethylamino)phenyl]methylene]-2,5-cyclohexadien-1-ydilene]-N-methyl-,bis[tetraphenylborate(1-)], Methanaminium Benzo[a]phenoxazin-7-ium, Methanaminium, N-[4-[[9-(dimethylamino)benzo[a]phenoxazin-7-ium-5-yl][4-(dimethylamino)phenyl]methylene]-2,5-cyclohexadien-1-ydilene]-N-methyl-,

[4-(α-3-Bromobenzo[b]thien-2-yl-p-dimethylamonobenzylidene)-2,5-cyclohexadien-1-ylidene]dimethylammonium chloride,

[4-(α-3-Chlorobenzo[b]thien-2-yl-p-dimethylaminobenzylidene)-2,5-cyclohexadien-1-ylidene]dimethylammonium chloride

[4-(p-Dimethylamino-α-3-methylbenzo[b]thien-2-ylbenzylidene)-2,5-cyclohexadien-1-ylidene]dimethylammonium chloride,

[4-[2-Bromo-α-(p-dimethylaminophenyl)-3-thenylidene]-2,5-cyclohexadien-1-ylidene]dimethylammonium chloride,

[4-[2-Chloro-α-(p-dimethylaminophenyl)-3-thenylidene]-2,5-cyclohexadien-1-ylidene]dimethylammonium chloride,

[4-[α-(p-Dimethylaminophenyl)-3-thenylidene]-2,5-cyclohexadien-1-ylidene]dimethylammonium chloride,

[4-[α-(p-Dimethylaminophenyl)-2,5-dimethyl-3-thenylidene]-2,5-cyclohexadien-1-ylidene]dimethylammonium chloride, Pyridinium, 1-[[4-(dimethylamino)phenyl][4-(dimethyliminio)-2,5-cyclohexadien-1-ylidene]methyl]-, bis[tetrafluoroborate(1-)], 2,5-Cyclohexadien-1-one, 2,3,5,6-tetrachloro-4-[(pentachlorophenyl)(2,3,5,6-tetrachloro-4-pyridinyl)methylene]-, Ethanaminium, N-[4-[[4-(diethylamino)phenyl](4-oxo-4H-1-benzothiopyran-3-yl)methylene]-2,5-cyclohexadien-1-ylidene]-N-ethyl-, perchlorate, Ethanaminium, N-[4-[[4-(diethylamino)phenyl](4-oxo-4H-1-benzothiopyran-3-yl)methylene]-2,5-cyclohexadien-1-ylidene]-N-ethyl-, 4H-1-Benzothiopyran, ethanaminium deriv, Benzenaminium, N-methyl-N-[4-[[4-methylphenylamino)phenyl](4-oxo-4H-1-benzothiopyran-3-yl)methylene]-2,5-cyclohexadien-1-ylidene]-, perchlorate Benzenaminium, N-methyl-N-[4-[[4-methylphenylamino)phenyl](4-oxo-4H-1-benzothiopyran-3-yl)methylene]-2,5-cyclohexadien-1-ylidene]-

Ethanaminium, N-[4-[[4-(diethylamino)-2-methylphenyl](4-oxo-4H-1-benzothiopyran-3-yl)methylene]-3-methyl-2,5-cyclohexadien-1-ylidene]-N-ethyl,perchlorate, Ethanaminium, N-[4-[[4-(diethylamino)-2-methylphenyl](4-oxo-4H-1-benzothiopyran-3-yl)methylene]-3-methyl-2,5-cyclohexadien-1-ylidene]-N-ethyl-, Ethanaminium 4H-1-Benzothiopyran, Methanaminium, N-[4-[[4-(dimethylamino)phenyl][5-(4-iodophenyl)-2-furanyl]methylene]-2,5-cyclohexadien-1-ylidene]-N-methyl-, chloride, Methanaminium, N-[4-[[5-(4-bromophenyl)-2-furanyl][4-(dimethylamino)phenyl]methylene]-2,5-cyclohexadien-1-ylidene]-N-methyl-, chloride, Methanaminium, N-[4-[[4-(dimethylamino)phenyl][5-(4-nitrophenyl)-2-furanyl]methylene]-2,5-cyclohexadien-1-ylidene]-N-methyl-, chloride,

[Oxybis[methylene-5,2-furandiyl[p-(N-methylanilino)benzylidyne]-2,5-cyclohexadien-4,1-diylidene]]bis[methylphenylammonium chloride],

[Oxybis[methylene-5,2-furandiyl[p-(N-methylanilino)benzylidyne]-2,5-cyclohexadien-4,1-diylidene]]bis[methylphenylammonium hydrogenosulfate], Benzenaminium, N,N'-[oxybis[methylene-5,2-furandiyl[[4-(methylphenylamino)phenyl]methylidyne]-2,5-cyclohexadien-4,1-diylidene]]bis[N-methyl]-, 1,4-Cyclohexadien-1-sulfonic acid and, 3-[4-anilino-α-(1-methyl-2-phenylindol-3-yl)-3-sulfobenzylidene]-6-phenylimino-salt, Trifluoromethane sulfonic acid and Pyridinium, 1-[[4-(dimethylamino)phenyl][4-(dimethyliminio)-2,5-cyclohexadien-1-ylidene]methyl]salt, Trifluoromethane sulfonic acid and 1-[[4-(dimethylamino)phenyl][4-dimethyliminio)-2,5-cyclohexadien-1-ylidene]methyl]pyridinium salt, Pyridinium, 1-[[4-(dimethylamino)phenyl][4-(dimethyliminio)-2,5-cyclohexadien-1-ylidene]methyl]-,

[4-[p-(Dimethylamino)-α-(9-methylcarbazol-3-yl)benzylidene]-2,5-cyclohexadien-1-ylidene]dimethylammonium chloride,

[4-[α-[p-(Dimethylamino)phenyl]furfurylidene]-2,5-cyclohexadien-1-ylidene]dimethylammonium chloride, Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-,perchlorate, diperchlorate, Methanaminium, N-[4-[bis(1,2,3,4,10,14b-hexahydro-2-methyldibenzo[c,f]pyrazino[1,2-a]azepin-8-yl)methylene]2,5-cyclohexadien-1-ylidene]-N-methyl-, perchlorate, Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-1H-Indolizinium, 3-[[4-(dimethyliminio)-2,5-cyclohexadien-1-ylidene](4-methoxyphenyl)methyl]-2-(2-hydroxy-5-methylphenyl)-1-methyl-, 1H-Indolizinium, 3-[[4-(dimethyliminio)-2,5-cyclohexadien-1-ylidene]phenylmethyl]-2-(2-hydroxy-5-methylphenyl)-1-methyl-, 1H-Indolizinium, 3-[[4-(dimethylamino)phenyl][4-(dimethyliminio)-2,5-cyclohexadien-1-ylidene]methyl]-2-(2-hydroxy-5-methylphenyl)-1-methyl-, 1H-Indolizinium, 3-[[4-(dimethylamino)phenyl][4-(dimethyliminio)-2,5-cyclohexadien-1-ylidene]methyl]-2-(2-hydroxy-5-methylphenyl)-1-methyl-, 1(Propanaminium, N-[4-[2-benzofuranyl[3-chloro-4-[ethyl(3-sulfopropyl)amino]phenyl]methylene]-2-chloro-2,5-cyclohexadien-1-ylidene]-N-ethyl-3-sulfo-, internal salt, sodium salt, 1-Propanaminium, N-[4-[2-benzofuranyl[4-[ethyl(3-sulfopropyl)amino]-3-methylphenyl]methylene]-2-methyl-2,5-cyclohexadien-1-ylidene]-N-ethyl-3-, 1-Butanaminium, N-[4-[2-benzofuranyl[4-[ethyl(4-sulfobutyl)amino]phenyl]methylene]-2,5-cyclohexadien-1-ylidene]-N-ethyl-4-, 1-Propanaminium, N-[4-[(5-chlorobenzo[b]thien-2-yl)[4-[methyl(3-sulfopropyl)amino]phenyl]methylene]-2,5-cyclohexadien-1-ylidene]-N-methyl-3-sulfo-, 1-Propanaminium, N-[4-[(3-chlorobenzo[b]thien-2-yl)[4-[methyl(3-sulfopropyl)amino]phenyl]methylene]-2,5-cyclohexadien-1-ylidene]-N-methyl-3-sulfo, sodium salt, 1-Propanaminium, N-[4-[Benzo[b]thien-2-yl[4-[methyl(3-sulfopropyl)amino]phenyl]methylene]-2,5-cyclohexadien-1-ylidene]-N-methyl-3-sulfo-, sodium salt, 1-Propanaminium, N-methyl-N-[4-[(3-methylbenzo[b]thien-2-yl)[4-[methyl(3-sulfopropyl)amino]phenyl]methylene]-2,5-cyclohexadien-1-ylidene]-3-sulfo-, sodium salt, 1-Propanaminium, N-[4-[(3-bromobenzo[b]thien-2-yl)[4-[methyl(3-sulfopropyl)amino]phenyl]methylene]-2,5-cyclohexadien-1-ylidene]-N-methyl-3-sulfo-, sodium salt, 1-Propanaminium, N-[4-[(6-chlorobenzo[b]thien-2-yl)[4-[methyl(3-sulfopropyl)amino]phenyl]methylene]-2,5-cyclohexadien-1-ylidene]-N-methyl-3-sulfo-, sodium salt 1-Propanaminium, N-methyl-N-[4-[[4-[methyl(3-sulfopropyl)amino]phenyl](5-nitro-2-benzofuranyl)methylene]-2,5-cyclohexadien-1-ylidene]-3-sulfo-, sodium salt, 1-Propanaminium, N-methyl-N-[4-[(5-methyl-2-benzofuranyl)[4-(methyl(3-sulfopropyl)amino]phenyl]methylene]-2,5-cyclohexadien-1-ylidene]-3-sulfo-, sodium salt, 1-Propanaminium, N-[4-[(5-chloro-2-benzofuranyl)[4-[methyl(3-sulfopropyl)amino]phenyl]methylene]-2,5-cyclohexadien-1-ylidene]-N-methyl-3-sulfo-, sodium salt, 1-Propanaminium, N-[4-[2-benzofuranyl[4-[methyl(3-sulfopropyl)amino]phenyl]methylene]-2,5-cyclohexadien-1-ylidene]-N-methyl-3-sulfo-, internal salt, sodium salt, Ethanaminium, N-[4-[(2-chlorophenyl)(1-methyl-2-phenyl-1H-indol-3-yl)methylene]-2,5-cyclohexadien-1-ylidene]-N-ethyl-, trichlorozincate(1-), Zincate(1-), trichloro-, N-[4-[(2-chlorophenyl)(1-methyl-2-phenyl-1H-indol-3-yl)methylene]-2,5-cyclohexadien-1-ylidene]-N-ethylethanaminium, Benzenesulfonic acid, 5-[(1,2-dimethyl-1H-indol-3-yl)[4-[(2-methylphenyl)imino]-3-sulfo-2,5-cyclohexadien-1-ylidene]methyl]-2-[(2-methylphenyl)amino]-, monosodium salt, Ethanaminium, N-[4-[(2-chlorophenyl)(1-methyl-2-phenyl-1H-indol-3-yl)methylene]-2,5-cyclohexadien-1-ylidene]-N-ethyl-, methyl sulfate, 3H-Pyrazol-3-one, 1,2-dihydro-4-[(4-hydroxy-3-methoxyphenyl)(3-methoxy-4-oxo-2,5-cyclohexadien-1-ylidene)methyl]-1,5-dimethyl-2-phenyl-, ion(1-), Ethanaminium, N-[4-[(2-chlorophenyl)(1-methyl-2-phenyl-1H-indol-3-yl)methylene]-2,5-cyclohexadien-1-ylidene]-N-ethyl-, acetate, Ethanaminium, N-[4-[(2-chlorophenyl)(1-methyl-2-phenyl-1H-indol-3-yl)methylene]-2,5-cyclohexadien-1-ylidene]-N-ethyl-, phosphate (1:1), Ethanaminium, N-[4-[(2-chlorophenyl)(1-methyl-2-phenyl-1H-indol-3-yl)methylene]-2,5-cyclohexadien-1-ylidene]-N-ethyl-, Ethanaminium, N-[4-[(2-chlorophenyl)(1-methyl-2-phenyl-1H-indol-3-yl)methylene]-2,5-cyclohexadien-1-ylidene]-N-ethyl-, chloride, compound with zinc chloride ($ZnCl_2$), N-[4-[(2-chlorophenyl)(1-methyl-2-phenyl-1H-indol-3-yl)methylene]-2,5-cyclohexadien-1-ylidene]-N-ethylethanaminium chloride, 1-Piperidinyloxy, 4-[[3,5-bis(1,1-dimethylethyl)-4-oxo-2,5-cyclohexadien-1-ylidene][3,5-bis(1,1-dimethylethyl)-4-oxyphenyl]methyl]-2,2,6,6-tetramethyl-1H-Pyrrol-1-yloxy, 3-[[3,5-bis(1,1-dimethylethyl)-4-oxo-2,5-cyclohexadien-1-ylidene][3,5-bis(1,1-dimethylethyl)-4-oxyphenyl]methyl]-2,5-dihydro-2,2,5,5-tetramethyl-, 1H-Pyrrol-1-yloxy, 3-[[3,5-bis(1,1-dimethylethyl)-4-hydroxyphenyl][3,5-bis(1,1-dimethylethyl)-4-oxo-2,5-cyclohexadien-1-ylidene]methyl]-2,5-dihydro-2,2,5,5-tetramethyl-, 1-Pyperidinyloxy, 4-[[3,5-bis(1,1-dimethylethyl)-4-hydroxyphenyl][3,5-bis(1,1-dimethylethyl)-4-oxo-2,5-cyclohexadien-1-ylidene]methyl]-2,2,6,6-tetramethyl-, Acetamide, N-methyl-N-[[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-, Carbamic acid [[2-[(3,5-dimethoxy-4-oxo-2,5-cyclohexadien-1-ylidene)(2,3,6,7-tetrahydro-1H,5H-benzo[ij]quinolizin-9-yl)methyl]phenyl]sulfonyl]methyl-,2-(methylsulfonyl)ethyl ester, Carbamic acid methyl[[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl 2-cyanoethyl ester, Carbamic acid methyl [[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-,2-(methylsulfonyl)ethylester, Carbamic acid methyl [[2-[[4-oxo-3-[2,2,2-trifluoro-1-hydroxy-1-(trifluoromethyl)ethyl]-1(4H)-naphthalenylidene](2,3,6,7-tetrahydro-1H,5H-benzo[ij]quinolizin-9-yl)methyl]phenyl]sulfonyl]-,2-(phenylsulfonyl) ethyl ester, Acetamide, N-[[2-[(3,5-dimethyl-4-oxo-2,5-cyclohexadien-1-ylidene)(2,3,6,7-tetrahydro-1H,5H-benzo[ij]quinolizin-9-yl)methyl]phenyl]sulfonyl]-N-methyl-2,5-Cyclohexadien-1-one, 4-[(4-hydroxy-3,5-dimethylphenyl)(2,3,5,6,8,9,11,12-octahydro-1,4,7,10,13-benzopentaoxacyclopentadecin-15-yl)methylene]-2,6-dimethyl-, Phenoxy, 4-[[3,5-bis(1,1-dimethylethyl)-4-oxo-2,5-cyclohexadien-1-ylidene](2,3,5,6,8,9,11,12-octahydro-1,4,7,10,13-benzopentaoxacyclopentadecin-15-yl)methyl]-2,6-bis(1,1-dimethylethyl)-, Ethanaminium, N-[4-[(2-chlorophenyl)(1-methyl-2-phenyl-1H-indol-3-yl)methylene]-2,5-cyclohexadien-1-ylidene]-N-ethyl-, chloride, Phenoxy, 4-[[3,5-bis(1,1-dimethylethyl)-4-oxo-2,5-cyclohexadien-1-ylidene]-3-pyridinylmethyl]-2,6-bis(1,1-dimethylethyl)-, 2,5-Cyclohexadien-1-one,4-[[3,5-bis(1,1-dimethylethyl)-4-hydroxyphenyl]-3-pyridinylmethylene]-2,6-bis(1,1-dimethylethyl)-,ion(1-), 2,5-Cyclohedaxien-1-one,4-[[3,5-bis(1,1-dimethylethyl)-4-hydroxyphenyl]-3-pyridinylmethylene]-2,6-bis(1,1-dimethylethyl)-, Phenoxy, 4,4'-[3,5-pyridinediylbis[[3,5-bis(1,1-dimethylethyl)-4-oxo-2,5-cyclohexadien-1-ylidene]methylene]] bis-2,6-bis(1,1-dimethylethyl)-, Phenoxy,4,4'-[2,4-pyridinediylbis[[3,5-bis(1,1-dimethylethyl)-4-oxo-2,5-cyclohexadien-1-ylidene]methylene]] bis-2,6-bis(1,1-dimethylethyl)-, Phenoxy, 4,4'-[2,5-pyridinediylbis[[3,5-bis(1,1-dimethylethyl)-4-oxo-2,5-cyclohexadien-1-ylidene]methylene]] bis-2,6-bis(1,1-dimethylethyl)-, Methanaminium, N-[4-[9H-carbazol-3-yl[4-(dimethylamino)phenyl]methylene]-2,5-cyclohexadien-1-ylidene]-N-methyl-, chloride,

[4-[α-Carbazol-3-yl-p-(dimethylamino)benzylidene]-2,5-cyclohexadien-1-ylidene]dimethylammonium chloride, Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene]-, acetate, Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene], (2,5-Cyclohexadien-1-one, 4,4'-[3,5-pyridinediylbis[(3,5-bis(1,1-dimethylethyl)-4-hydroxyphenyl]methylidyne]]bis[2,6-bis(1,1-dimethylethyl)-, ion(2-)-, 2,5-Cyclohexadien-1-one, 4,4'-[2,6-pyridinediylbis[[3,5-bis(1,1-dimethylethyl)-4-hydroxyphenyl]methylidyne]]bis-2,6-bis(1,1-dimethylethyl)-, ion(2-), 2,5-Cyclohexadien-1-one, 4,4'-[2,5-pyridinediylbis[[3,5-bis(1,1-dimethylethyl)-4-hydroxyphenyl]methylidyne]]bis-2,6-bis(1,1-dimethylethyl)-, ion(2-)-, 2,5-Cyclohexadien-1-one, 4,4'-[2,4-pyridinediylbis[[3,5-bis(1,1-dimethylethyl)-4-hydroxyphenyl]methylidyne]]bis-2,6-bis(1,1-dimethylethyl)-, ion(2-)-, 2,5-Cyclohexadien-1-one, 4,4'-[3,5-pyridinediylbis[[3,5-bis(1,1-dimethylethyl)-4-hydroxyphenyl]methylidyne]]bis-2,6-bis(1,1-dimethylethyl)-, 2,5-Cyclohexadien-1-one, 4,4'-[2,5-pyridinediylbis[[3,5-bis(1,1-dimethylethyl)-4-hydroxyphenyl]methylidyne]]bis-2,6-bis(1,1-dimethylethyl)-, 2,5-Cyclohexadien-1-one, 4,4'-[2,4-pyridinediylbis[[3,5-bis(1,1-dimethylethyl)-4-hydroxyphenyl]methylidyne]]bis-2,6-bis-1,1-dimethylethyl)-, Cyclohexanaminium, N-methyl-N-[4-[(2-methyl-1H-indol-3-yl)phenylmethylene]-2,5-cyclohexadien-1-ylidene]-, trichlorozincate(1-), Zincate(1-), trichloro-, N-methyl-N-[4-[(2-methyl-1H-indol-3-yl)phenylmethylene]-2,5-cyclohexadien-1-ylidene]cyclohexanaminium,
Cyclohexanaminium, N-methyl-N-[4-[(2-methyl-1H-indol-3-yl)phenylmethylene]-2,5-cyclohexadien-1-ylidene]-,
Cyclohexanaminium, N-[4-[(2-chlorophenyl)(1-methyl-2-phenyl-1H-indol-3-yl)methylene]-2,5-cyclohexadien-1-ylidene]-N-methyl-, trichlorozincate(1-),
Zincate(1-), trichloro-, N-[4-[(2-chlorophenyl)-(1-methyl-2-phenyl-1H-indol-3-yl)methylene]-2,5-cyclohexadien-1-ylidene]-N-methylcyclohexanaminium,
Cyclohexanaminium, N-[4-[(2-chlorophenyl)(1-methyl-2-phenyl-1H-indol-3-yl)methylene]-2,5-cyclohexadien-1-ylidene]-N-methyl-,
Cyclohexanaminium, N-[4-[(2-chlorophenyl)[2-(4-chlorophenyl)-1-methyl-1H-indol-3-yl]methylene]-2,5-cyclohexadien-1-ylidene]-N-methyl-, trichlorozincate(1-),
N-[4-[(2-chlorophenyl)[2-(4-chlorophenyl)-1-methyl-1H-indol-3-yl]methylene]2,5-cyclohexadien-1-ylidene]-N-methylcyclohexanaminium trichlorozincate,
Cyclohexanaminium, N-[4-[(2-chlorophenyl)[2-(4-chlorophenyl)-1-methyl-1H-indol-3-yl]methylene]-2,5-cyclohexadien-1-ylidene]-N-methyl-,
Benzenemethanaminium, N-cyclohexyl-N-[4-[[1-(2-ethoxyethyl)-2-phenyl-1H-indol-3-yl](4-methylphenyl)methylene]-2,5-cyclohexadien-1-ylidene]-, trichlorozincate(1-),
N-cyclohexyl-N-[4-[[1-(2-ethoxyethyl)-2-phenyl-1H-indol-3-yl](4-methylphenyl)methylene]-2,5-cyclohexadien-1-ydilene]benzenemethanaminium trichlorozincate,
Benzenemethanaminum, N-cyclohexyl-N-[4-[[1-(2-ethoxyethyl)-2-phenyl-1H-indol-3-yl](4-methylphenyl)methylene]-2,5-cyclohexadien-1-ylidene]-,
Cyclohexanaminium, N-methyl-N-[4[(1-methyl-2-phenyl-1H-indol-3-yl)phenylmethylene]-2,5-cyclohexadien-1-ylidene]-, trichlorozincate(1-),
N-methyl-N[4-[(1-methyl-2-phenyl-1H-indol-3-yl)phenylmethylene]-2,5-cyclohexadien-1-ylidene]cyclohexanaminium trichlorozincate,
Cyclohexanaminium, N-methyl-N-[4-[(1-methyl-2-phenyl-1H-indol-3-yl)phenylmethylene]-2,5-cyclohexadien-1-ylidene]-,
Cyclohexanaminium, N-[4-[(2-bromophenyl)(1,2-dimethyl-1H-indol-3-yl)methylene]-2,5-cyclohexadien-1-ylidene]-N-ethyl-, trichlorozincate(1-),
N-[4-[(2-bromophenyl)(1,2-dimethyl-1H-indol-3-yl)methylene]-2,5-cyclohexadien-1-ylidene]-N-ethylcyclohexanaminium trichlorozincate,
Cyclohexanaminium, N-[4-[(2-bromophenyl)(1,2-dimethyl-1H-indol-3-yl)methylene]-2,5-cyclohexadien-1-ylidene]-N-ethyl-,
Ethanaminium, N-[3-chloro-4-[(1-methyl-2-phenyl-1H-indol-3-yl)phenylmethylene]-2,5-cyclohexadien-1-ylidene]-N-ethyl-, sulfate (1:1),
Ethanaminium, N-[3-chloro-4-[(1-methyl-2-phenyl-1H-indol-3-yl)phenylmethylene]-2,5-cyclohexadien-1-ylidene]-N-ethyl-,
Ethanaminium, N-ethyl-N-[4-[(2-methyl-1H-indol-3-yl)(2-nitrophenyl)methylene]-2,5-cyclohexadien-1-ylidene]-, sulfate (1:1),
Ethanaminium, N-ethyl-N-[4-[(2-methyl-1H-indol-3-yl)(2-nitrophenyl)methylene]-2,5-cyclohexadien-1-ylidene]-,
Methanamine, N-[4-[(1-methyl-2-phenyl-1H-indol-3-yl)phenylmethylene]-2,5-cyclohexadien-1-ylidene]-, sulfate (1:1),
Methanamine, N-4-[(1-methyl-2-phenyl-1H-indol-3-yl)phenylmethylene]-2,5-cyclohexadien-1-ylidene]-,
Methanaminium, N-[4-[[4-(dimethylamino)phenyl]-2-furanylmethylene]-2,5-cyclohexadien-1-ylidene]-N-methyl-, (T-4)-tetrabromothallate(1-),
Thallate(1-), tetrabromo-, (T-4), N-[4-[[4-(dimethylamino)phenyl]-2-furanylmethylene]-2,5-cyclohexadien-1-ylidene]-N-methylmethanaminium,
Phenoxy, 4-[[3,5-bis(1,1-dimethylethyl)-4-oxo-2,5-cyclohexadien-1-ylidene][6-[[3,5-bis(1,1-dimethylethyl)-4-oxo-2,5-cyclohexadien-1-ylidene][3,5-bis(1,1-dimethylethyl)-2,5-cyclohexadien-1-one, 4-4,4'-[2,6-pyridinediylbis[[3,5-bis(1,1-dimethylethyl)-4-hydroxyphenyl]methylidyne]]bis-2,6-bis(1,1-dimethylethyl)-,
Methanaminium, N-[4-[(2,3-dihydro-1,5-dimethyl-3-oxo-2-phenyl-1H-pyrazol-4-yl)(3-nitrophenyl)methylene]-2,5-cyclohexadien-1-ylidene]-N-methyl-, chloride,
Methanaminium, N-[4-[(3-bromophenyl)(2,3-dihydro-1,5-dimethyl-3-oxo-2-phenyl-1H-pyrazol-4-yl)methylene]-2,5-cyclohexadien-1-ylidene]-N-methyl-, chloride,
Methanaminium, N-[4-[(2,3-dihydro-1,5-dimethyl-3-oxo-2-phenyl-1H-pyrazol-4-yl)(3-methoxyphenyl)methylene]-2,5-cyclohexadien-1-ylidene]-N-methyl-, chloride,
Methanaminium, N-[4-[(2,3-dihydro-1,5-dimethyl-3-oxo-2-phenyl-1H-pyrazol-4-yl)phenylmethylene]-2,5-cyclohexadien-1-ylidene]-N-methyl-, chloride,
[[4-[(1-methyl-2-phenyl-1H-indol-3-yl)[4-[(sulfophenyl)amino]phenyl]methylene]-2,5-cyclohexadien-1-ylidene]amino]-,
Methanaminium, N-[4-[(2,3-dihydro-1,5-dimethyl-3-oxo-2-phenyl-1H-pyrazol-4-yl)[4-(dimethylamino)phenyl]methylene]-2,5-cyclohexadien-1-ydilene]-N-methyl-,chloride,
Benzenamine, 4-[(2-[1,1'-biphenyl]-4-yl-1-butyl-1H-indol-3-yl)[4-[(4-ethoxyphenyl)imino]-2,5-cyclohexadien-1-ylidenemethyl]-N-(4-ethoxyphenyl),
Benzenaminium, N-methyl-N-[4-[[4-(methylphenylamino)phenyl](4-oxo-4H-1-benzopyran-3-yl)methylene]-2,5-cyclohexadien-1-ylidene]-,
Ethanaminium, N-[4-[[4-(diethylamino)phenyl](4-oxo-4H-1-benzopyran-3-yl)methylene]-2,5-cyclohexadien-1-ylidene]-N-ethyl-,
Benzenaminium, 4-ethoxy-N-methyl-N-[4-[(1-methyl-2-phenyl-1H-indol-3-yl)phenylmethylene]-2,5-cyclohexadien-1-ylidene], chloride,
Methanaminium, N-[4-[12H-benzo[a]phenoxazin-5-yl[4-(dimethylamino)phenyl]methylene]-2,5-cyclohexadien-1-ylidene]-N-methyl-, chloride,
Benzenaminium, N-methyl-N-[4-[(1-methyl-2-phenyl-1H-indol-3-yl)phenylmethylene]-2,5-cyclohexadien-1-ylidene]-,
Ethanaminium, N-[4-[[4-(diethylamino)phenyl](7-methoxy-2,1,3-benzothiadiazol-4-yl)methylene]-2,5-cyclohexadien-1-ylidene]-N-ethyl-,
Ethanaminium, N-[4-[[4-(diethylamino)phenyl](5-methoxy-2,1,3-benzothiadiazol-4-yl)methylene]-2,5-cyclohexadien-1-ylidene]-N-ethyl-,
Ethanaminium, N-[4-[[4-(diethylamino)phenyl](7-methyl-2,1,3-benzothiadiazol-4-yl)methylene]-2,5-cyclohexadien-1-ylidene]-N-ethyl-, Ethanaminium, N-[4-[2,1,3-benzothiadiazol-5-yl[4-(diethylamino)phenyl]methylene]-2,5-cyclohexadien-1-ylidene]-N-ethyl-, Ethanaminium, N-[4-[2,1,3-benzothiadiazol-4-yl[4-(diethylamino)phenyl]methylene]-2,5-cyclohexadien-1-ylidene]-N-ethyl-, Methanaminium, N-methyl-N-[4-[(1-methyl-2-phenyl-1H-indol-3-yl)phenylmethylene]-2,5-cyclohexadien-1-ylidene]-, chloride, Methanaminium, N-methyl-N-[4-[(1-methyl-2-phenyl-1H-indol-3-yl)phenylmethylene]-2,5-cyclohedaxien-1-ylidene]-, Methanaminium, N-[4-[[4-(dimethylamino)phenyl](7-methoxy-2,1,3-benzothiadiazol-4-yl)methylene]-2,5-cyclohexadien-1-ylidene]-N-methyl-, Methanaminium, N-[4-[[4-(dimethylamino)phenyl](5-methoxy-2,1,3-benzothiadiazol-4-yl)methylene]-2,5-cyclohexadien-1-ylidene]-N-methyl-, Methanaminium, N-[4-[[4-(dimethylamino)phenyl](7-methyl-2,1,3-benzothiadiazol-4-yl)methylene]-2,5-cyclohexadien-1-ylidene]-N-methyl-, Methanaminium, N-[4-[2,1,3-benzothiadiazol-5-yl[4-dimethylamino)phenyl]methylene]-2,5-cyclohexadien-1-ylidene]-N-methyl-, Methanaminium, N-[4-[2,1,3-benzothiadiazol-4-yl[4-(dimethylamino)phenyl]methylene]-2,5-cyclohexadien-1-ylidene]-N-methyl-, Methanaminium, N-[4-[[4-(dimethylamino)phenyl]-3-pyridinylmethylene]-2,5-cyclohexadien-1-ylidene]-N-ethyl-, Methanaminium, N-[4-[[4-(dimethylamino)phenyl]-4-pyridinylmethylene]-2,5-cyclohexadien-1-ylidene]-N-methyl-, Methanaminium, N-[4-[[4-(dimethylamino)phenyl]-2-thienylmethylene]-2,5-cyclohexadien-1-ylidene]-N-methyl, Methanaminium, N-[4-[[4-(dimethylamino)phenyl]-2-furanylmethylene]-2,5-cyclohexadien-1-ylidene]-N-methyl-, Methanaminium, N-[4-[[4-(dimethylamino)phenyl]-3-thienylmethylene]-2,5-cyclohexadien-1-ylidene]-N-methyl-[[4-[(1-methyl-2-phenyl-1H-indol-3-yl)[4-[(sulfophenyl)amino]phenyl]methylene]-2,5-cyclohexadien-1-ylidene]amino]-, Ethoxy[[4-[[4-[(ethoxysulfophenyl)amino]phenyl](1-methyl-2-phenyl-1H-indol-3-yl)methylene]-2,5-cyclohexadien-1-ylidene]amino]-, Benzenamine, N-methyl-4-[[4-(methylimino)-2,5-cyclohedaxien-1-ylidene](2-methyl-1H-indol-3-yl)methyl]-, Methanaminium, N-[4-[[4-(dimethylamino)phenyl](2-methyl-1H-indol-3-yl)methylene]-2,5-cyclohexadien-1-ylidene]-N-methyl-, Benzenamine, N-methyl-4-[[4-(methylimino)-2,5-cyclohexadien-1-ylidene](1-methyl-2-phenyl-1H-indol-3-yl)methyl]-, conjugated monoacid, Methanaminium, N-[4-[[4-(dimethylamino)phenyl](1-methyl-2-phenyl-1H-indol-3-yl)methylene]-2,5-cyclohexadien-1-ylidene]-N-methyl-, Benzenamine, 4-ethoxy-N-[4-[[4-[(4-ethoxyphenyl)amino]phenyl](2-phenyl-1H-indol-3-yl)methylene]-2,5-cyclohexadien-1-ylidene]-, Benzenamine, 4-ethoxy-N-[4-[[4-[(4-ethoxyphenyl)amino]phenyl](2-methyl-1H-indol-3-yl)methylene]-2,5-cyclohexadien-1-ylidene]-, Benzenamine, N-[4-[(1,2-dimethyl-1H-indol-3-yl)[4-[(4-ethoxyphenyl)amino]phenyl]methylene]-2,5-cyclohexadien-1-ylidene]-4-ethoxy-, Benzenamine, 4-[(1-methyl-2-phenyl-1H-indol-3-yl)[4-(phenylimino)-2,5-cyclohexadien-1-ylidene]methyl]-N-phenyl-, conjugated monoacid, Benzenamine, 4-ethoxy-N-[4-[[4-[(4-ethoxyphenyl)amino]phenyl](1-methyl-2-phenyl-1H-indol-3-yl)methylene]-2,5-cyclohexadien-1-ylidene]-, Methanaminium, N-[4-[[4-(dimethylamino)phenyl](2-phenyl-1H-indol-3-yl)methylene]-2,5-cyclohexadien-1-ylidene]-N-methyl-, Benzenaminium, N-methyl-N-[4-[[4-(methylphenylamino)phenyl](4-oxo-4H-1-benzopyran-3-yl)methylene]-2,5-cyclohexadien-1-ylidene]-, chloride, Benzenaminium, N-methyl-N-[4-[[4-(methylphenylamino)phenyl](4-oxo-4H-1-benzopyran-3-yl)methylene]-2,5-cyclohexadien-1-ylidene]-, perchlorate, Ethanaminium, N-[4-[[4-(diethylamino)phenyl](4-oxo-4H-1-benzopyran-3-yl)methylene]-2,5-cyclohexadien-1-ylidene]-N-ethyl-, perchlorate, Ethanaminium, N-[4-[[4-(diethylamino)phenyl](4-oxo-4H-1-benzopyran-3-yl)methylene]-2,5-cyclohexadien-1-ylidene]-N-ethyl-, chloride, Benzenaminium, N-methyl-N-[4-[[4-(methylphenylamino)phenyl](4-oxo-4H-1-benzopyran-3-yl)methylene]-2,5-cyclohexadien-1-ylidene]-, acetate, Ethanaminium, N-[4-[[4-(diethylamino)phenyl](4-oxo-4H-1-benzopyran-3-yl)methylene]-2,5-cyclohexadien-1-ylidene]-N-ethyl-, acetate, Methanaminium, N-[4-[(2,3-dihydro-1,5-dimethyl-3-oxo-2-phenyl-1H-pyrazol-4-yl)(3-nitrophenyl)methylene]-2,5-cyclohexadien-1-ylidene]-N-methyl-, Methanaminium, N-[4-[(3-bromophenyl)(2,3-dihydro-1,5-dimethyl-3-oxo-2-phenyl-1H-pyrazol-4-yl)methylene]-2,5-cyclohexadien-1-ylidene]-N-methyl-, Methanaminium, N-[4-[(2,3-dihydro-1,5-dimethyl-3-oxo-2-phenyl-1H-pyrazol-4-yl)(3-methoxyphenyl)methylene]-2,5-cyclohexadien-1-ylidene]-N-methyl-, Methanaminium, N-[4-[(2,3-dihydro-1,5-dimethyl-3-oxo-2-phenyl-1H-pyrazol-4-yl)phenylmethylene]-2,5-cyclohexadien-1-ylidene]-N-methyl-, Methanaminium, N-[4-[(2,3-dihydro-1,5-dimethyl-3-oxo-2-phenyl-1H-pyrazol-4-yl)(3-methylphenyl)methylene]-2,5-cyclohexadien-1-ylidene]-N-methyl-, Benzenamine, N-[4-[(1-ethyl-2-phenyl-1H-indol-3-yl)[4-[(2-methoxyphenyl)amino]phenyl]methylene]-2,5-cyclohexadien-1-ylidene]-2-methoxy-, monochlorhydrate 2-hydroxy-5-[[4-[[4-[(4-hydroxy-3-sulfophenyl)amino]phenyl](1-methyl-2-phenyl-1H-indol-3-yl)methylene]-2,5-cyclohexadien-1-ylidene]amino]-, Benzenamine, 2-ethoxy-N-[4-[[-4-(2-ethoxyphenyl)amino]phenyl](1-methyl-2-phenyl-1H-indol-3-yl)methylene]-2,5-cyclohexadien-1-ylidene]-, monochlorhydrate, Methanaminium, N-[4-[[4-(dimethylamino)phenyl]-2-furanylmethylene]-2,5-cyclohexadien-1-ylidene]-N-methyl-, perchlorate 2-ethoxy-5-[[4-[[4-[(4-ethoxy-3-sulfophenyl)amino]phenyl](1-methyl-2-phenyl-1H-indol-3-yl)methyl]-2,5-cyclohexadien-1-ylidene]amino]-, Ammonium, [4-[α-[p-(dimethylamino)phenyl]furfurylidene]-2,5-cyclohexadien-1-ylidene]dimethyl-,tetrachlorogallate(1-), Methanaminium, N-[4-[[4-(dimethylamino)phenyl]-2-thienylmethyl]-2,5-cyclohexadien-1-ylidene]-N-methyl-, perchlorate, Ammonium, [4-[p-(dimethylamino)-α-2-thienylbenzylidene]-2,5-cyclohexadien-1-ylidene]dimethyl-, perchlorate,
Ammonium, (2-cyanoethyl)[4-[α-[4-[(2-cyanoethyl)ethylamino]-o-tolyl]piperonylidene]-3-methyl-2,5-cyclohexadien-1-ylidene]ethyl-,
Ammonium, dimethyl[4-[α-(1-methyl-2-phenylindol-3-yl)benzylidene]-2,5-cyclohexadien-1-ylidene]-, chloride,
Ammonium, (p-ethoxyphenyl)methyl[4-[α-(1-methyl-2-phenylindol-3-yl)benzylidene]-2,5-cyclohexadien-1-ylidene]-, chloride,
(p-ethoxyphenyl)methyl[4-[α-(1-methyl-2-phenylindol-3-yl)benzylidene]-2,5-cyclohexadien-1-ylidene]ammonium chloride,
Ammonium, [4-[α-2,1,3-benzothiadiazol-4-yl-p-(dimethylamino)benzylidene]-2,5-cyclohexadien-1-ylidene]dimethyl-, perchlorate,
Ammonium, [4-[p-(dimethylamino)-α-(5-methoxy-2,1,3-benzothiadiazol-4-yl)benzylidene]-2,5-cyclohexadien-1-ylidene]dimethyl-, perchlorate,
Ammonium, [4-[p-(dimethylamino)-α-(5-methoxy-2,1,3-benzothiadiazol-4-yl)benzylidene]-2,5-cyclohexadien-1-ylidene]diethyl-, perchlorate,
Ammonium, [4-[p-(diethylamino)-α-(7-methoxy-2,1,3-benzothiadiazol-4-yl)benzylidene]-2,5-cyclohexadien-1-ylidene]diethyl-, perchlorate,
Ammonium, [4-[p-(diethylamino)-α-(7-methoxy-2,1,3-benzothiadiazol-4-yl)benzylidene]-2,5-cyclohexadien-1-ylidene]dimethyl-, perchlorate,
Ammonium, [4-[p-(diethylamino)-α-(7-methyl-2,1,3-benzothiadiazol-4-yl)benzylidene]-2,5-cyclohexadien-1-ylidene]diethyl-, perchlorate,
Ammonium, [4-[p-(dimethylamino)-α-(7-methyl-2,1,3-benzothiadiazol-4-yl)benzylidene]-2,5-cyclohexadien-1-ylidene]dimethyl-, perchlorate,
Ammonium, [4-[α-2,1,3 benzothiadiazol-4-yl-p(diethylamino)benzylidene]-2,5-cyclohexadien-1-ylidene]diethyl-, perchlorate,
Ammonium, [4-[α-2,1,3-benzothiadiazol-5-yl-p(diethylamino)benzylidene]-2,5-cyclohexadien-1-ylidene]diethyl-, perchlorate,
Ammonium, [4-[α-2,1,3 benzothiadiazol-5-yl-p(diethylamino)benzylidene]-2,5-cyclohexadien-1-ylidene] dimethyl-, perchlorate,
Ammonium, methyl [4-[α-(1-methyl-2-phenylindol-3-yl)benzylidene]-2,5-cyclohexadien-1-ylidene]phenyl-, trichlorozincate(1-),
Methyl [4-[α-(1-methyl-2-phenylindol-3-yl)benzylidene]-2,5-cyclohexadien-1-ylidene]phenylammonium trichlorozincate,
Dimethyl [4-[α-(1-methyl-2-phenylindol-3-yl)benzylidene]-2,5-cyclohexadien-1-ylidene]ammonium trichlorozincate,
Dimethyl [4-[α-(1-methyl-2-phenylindol-3-yl)benzylidene]-2,5-cyclohexadien-1-ylidene]ammonium trichlorozincate,
Indole, 3-[α-(4-imino-2,5-cyclohexadien-1-ylidene)benzyl]-1,2-dimethyl-, monohydrochloride,
Indole, 3-[α-[4-[(p-ethoxyphenyl)imino]-2,5-cyclohexadien-1-ylidene]benzyl]-1-methyl-2-phenyl-, monohydrochloride,
Ammonium, [4-[α-[9-(2-cyanoethyl)carbazol-3-yl]-p-(dimethylamino)benzylidene]-2,5-cyclohexadien-1-ylidene]dimethyl-,
Ammonium, [4-[α-carbazol-3-yl-p-(dimethylamino)benzylidene]-2,5-cyclohexadien-1-ylidene]dimethyl-,
Ammonium, [4-[α-[9-(2-cyanoethyl)carbazol-3-yl]benzylidene]-2,5-cyclohexadien-1-ylidene]dimethyl-,
Ammonium, [4-(α-carbazol-3-ylbenzylidene)-2,5-cyclohexadien-1-ylidene]dimethyl-,
2,5-cyclohexadien-1-one, 2,6-di-tert-butyl-4-(α-morpholinobenzylidene)-,
2,5-cyclohexadien-1-one, 2,6-di-tert-butyl-4-[α-(2,2-dimethyl-1-aziridinyl)benzylidene]-,
2,5-cyclohexadien-1-one,4-(α-1-aziridinylbenzylidene)-2,6-di-tert-butyl-,
2,5-cyclohexadien-1-one, 2,6-bis(1,1-dimethylethyl)-4-(phenyl-1-piperidinylmethylene)-,
2,5-cyclohexadien-1-one, 2,6-di-tert-butyl-4-(α-piperidinobenzylidene)-,
Ammonium, [4-[α-[4-(diethylamino)-o-tolyl]piperonyl]-3-methyl-2,5-cyclohexadien-1-ylidene]diethyl-, chloride,
Ammonium, [4-[α-[4-(diethylamino)-o-tolyl]-2-thenylidene]-3-methyl-2,5-cyclohexadien-1-ylidene]diethyl-, chloride,
Ammonium, [4-[α-[p-(diethylamino)phenyl]-5-nitrofurfurylidene]-2,5-cyclohexadien-1-ylidene]dimethyl-, chloride,
Ammonium, [4-[5-bromo-α-[p-diethylamino)phenyl]furfurylidene]-2,5-cyclohexadien-1-ylidene]diethyl-, chloride,
Ammonium, [4-[α-[p-(dimethylamino)phenyl]-2-furfurylidene]-2,5-cyclohexadien-1-ylidene]diethyl-, chloride
2-hydroxy-5-[[4-[[4-[ (4-hydroxy-3-sulfophenyl)amino]phenyl](1-methyl-2-phenyl-1H-indol-3-yl)methylene]-2,5-cyclohexadien-1-ylidene]amino]-,
Ammonium, [4-[α-12H-benzo[a]phenoxazin-5-yl-p-(dimethylamino)benzylidene]-2,5-cyclohexadien-1-ylidene]dimethyl, chloride, compound with zinc chloride,
[4-[α-12H-benzo[a]phenoxazin-5-yl-p-(dimethylamino)benzylidene]-2,5-cyclohexadien-1-ylidene]dimethylammonium chloride
Benzenamine, N,2-dimethyl-4-[(2-methyl-1H-indol-3-yl)[3-methyl-4-(methylimino)-2,5-cyclohexadien-1-ylidene]methyl]-, monohydrochloride,
Indole, 2-methyl-3-[3-methyl-4-(methylamino)-α-[3-methyl-4-(methylimino)-2,5-cyclohexadien-1-ylidene]benzyl]-monohydrochloride,
Methanaminium, N-[4-[[4-(dimethylamino)phenyl]-2-furanylmethylene]-2,5-cyclohexadien-1-ylidene]-N-methyl-, chloride,
Ammonium, [4-[α-[p-dimethylamino)phenyl]furfurylidene]-2,5-cyclohexadien-1-ylidene]dimethyl-, chloride,
Benzenaminium, N-[4-[[2-(4-chlorophenyl)-4,6-dimethyl-1-(2-methylpropyl)-1H-indol-3-yl](2,4-disulfophenyl)methylene]-2,5-cyclohexadien-1-ylidene]-4-methoxy-N-methyl-,
Ammonium, [4-[α-[2-(p-chlorophenyl)-1-isobutyl-4,6-dimethylindol-3-yl]-2,4-disulfobenzylidene]-2,5-cyclohexadien-1-ylidene](p-methoxyphenyl)methyl-, hydroxyde,
2-ethoxy-5-[[4-[[4-[(4-ethoxy-3-sulfophenyl)amino]phenyl](1-methyl-2-phenyl-1H-indol-3-yl)methylene]-2, 5-cyclohexadien-1-ylidene]amino]-,
5-[[3-carboxy-5-methyl-4-oxo-2,5-cyclohexadien-1-ylidene)(4,5-dihydro-3-methyl-5-oxo-1-phenyl-1H-pyrazol-4-yl)methyl]-2-hydroxy-3-methyl-, 5-[[4-[[2-(4-chlorophenyl)-4,6-dimethyl-1-(2-methylpropyl)-1H-indol-3-yl][4-[(4-ethoxy-3-sulfophenyl)amino]phenyl]methylene]-2,5-cyclohexadien-1-ylidene]amino]-2-ethoxy-,
N-[α-[2-(p-chlorophenyl)-1-isobutyl-4,6-dimethylindol-3-yl]-α-[4-[(4-ethoxy-3-sulfophenyl)imino]-2,5-cyclohexadien-1-ylidene]-p-tolyl]-6-ethoxy-,
6-[(4-ethoxyphenyl)imino]-3-[(1-methyl-2-phenyl-1H-indol-3-yl)[4-[(2-sulfoethyl)amino]phenyl]methylene]-,
6-[(p-ethoxyphenyl)imino]-3-[α-(1-methyl-2-phenylindol-3-yl)-p-[(2-sulfoethyl)amino]benzylidene]-,
Methanaminium, N-[4-[[4-(dimethylamino)phenyl]-3-thienylmethylene]-2,5-cyclohexadien-1-ylidene]-N-methyl-, perchlorate
[4-[α-[p-(Dimethylamino)phenyl]-3-thenylidene]-2,5-cyclohexadien-1-ylidene]dimethylammonium perchlorate,
Ammonium, [4-[α-[p-(dimethylamino)phenyl]furfurylidene]-2,5-cyclohexadien-1-ylidene]dimethyl-, bromide
[4-[α-[p-(Dimethylamino)phenyl]furfurylidene]-2,5-cyclohexadien-1-ylidene]dimethylammonium bromide,
Methanaminium, N-[4-[[4-(dimethylamino)phenyl]-3-pyridinylmethylene]-2,5-cyclohexadien-1-ylidene]-N-methyl-, perchlorate,
Ammonium, [4-[p-(dimethylamino)-α-3-pyridylbenzylidene]-2,5-cyclohexadien-1-ylidene]dimethyl-, perchlorate
[4-[p-(Dimethylamino)-α-3-pyridylbenzylidene]-2,5-cyclohexadien-1-ylidene]dimethylammonium perchlorate,
Ammonium, [4-[p-(dimethylamino)-α-4-pyridylbenzylidene]-2,5-cyclohexadien-1-ylidene]dimethyl-, perchlorate
[4-[p-(Dimethylamino)-α-4-pyridylbenzylidene]-2,5-cyclohexadien-1-ylidene]dimethylammonium perchlorate,
Ammonium, [4-[p-(dimethylamino)-α-2-pyridylbenzylidene]-2,5-cyclohexadien-1-ylidene]dimethyl-, chloride
[4-[p-(Dimethylamino)-α-2-pyridylbenzylidene]-2,5-cyclohexadien-1-ylidene]dimethylammonium chloride
and the addition salts thereof.

10. The composition according to claim 1, wherein the at least one dye is present in an amount ranging from approximately 0.0001% to approximately 10% by weight, relative to the total weight of the dye composition.

11. The composition according to claim 10, wherein the at least one dye is present in an amount ranging from approximately 0.005% to approximately 10% by weight, relative to the total weight of the dye composition.

12. The composition according to claim 11, wherein the at least one dye is present in an amount ranging from approximately 0.01% to approximately 6% by weight, relative to the total weight of the dye composition.

13. The composition according to claim 1, further comprising at least one additional direct dye different from the at least one dye chosen from formulae (I), (Ibis), (II) and (IIbis) and the tautomeric forms thereof and the addition salts thereof.

14. The composition according to claim 13, wherein the at least one additional direct dye is chosen from neutral, acid and cationic benzenic nitrated direct dyes; neutral, acid and cationic azoic direct dyes; quinonic direct dyes; azinic direct dyes; triarylmethanic direct dyes; indoaminic direct dyes; and natural direct dyes.

15. The composition according to claim 13, wherein the at least one additional direct dye is chosen from neutral, acid and cationic anthraquinonic direct coloring agents.

16. The composition according to claim 13, wherein the at least one additional direct dye is present in an amount ranging from approximately 0.001% to approximately 20% by weight, relative to the the total weight of the dye composition.

17. The composition according to claim 16, wherein the at least one additional direct dye is present in an amount ranging from approximately 0.005% to approximately 10% by weight, relative to the total weight of the dye composition.

18. The composition according to claim 1, further comprising at least one oxidation base and optionally at least one coupler.

19. The composition according to claim 18, wherein the at least one oxidation base is chosen from paraphenylenediamines, bisphenylalkylenediamines, para-aminophenols, ortho-aminophenols, heterocyclic bases and the addition salts thereof.

20. The composition according to claim 18, wherein the at least one coupler is chosen from metaphenylenediamine couplers, meta-aminophenol couplers, metadiphenol couplers, naphthalenic couplers, heterocyclic couplers and the addition salts thereof.

21. The composition according to claim 18, wherein the at least one oxidation base and/or the optional at least one coupler are each present in an amount ranging from approximately 0.001% to approximately 10% by weight, relative to the total weight of the composition.

22. The composition according to claim 21, wherein the at least one oxidation base and/or the optional at least one coupler are each present in an amount ranging from approximately 0.005% to approximately 6% by weight, of the total weight of the dye composition.

23. The composition according to claim 1, having a pH ranging from about 3 to about 12.

24. The composition according to claim 23, having a pH ranging from about 5 to about 11.

25. The composition according to claim 24, having a pH ranging from about 6 to about 8.5.

26. A method for direct dyeing of keratin fibers, comprising:
(A) applying to the keratin fibers at least one dye composition comprising, in a cosmetic medium suitable for dyeing, at least one dye chosen from formulae (I), (Ibis), (II) and (Ibis) and the tautomeric forms thereof and the addition salts thereof:

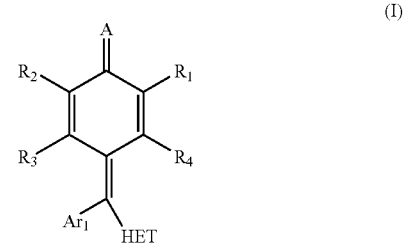

-continued

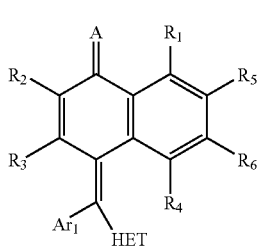
(Ibis)

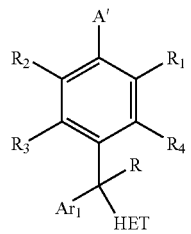
(II)

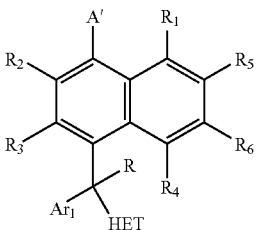
(IIbis)

wherein:

Ar₁, which may be identical or different, is chosen from aryl optionally substituted with at least one Z group;

HET, which may be identical or different, is chosen from heterocycles optionally substituted with at least one Z' group;

A, which may be identical or different, is chosen from O; NH; N-alkyl; N-hydroxyalkyl; ammonium, N-alkylammonium, N-(hydroxyalkyl)ammonium, N,N-dialkylammonium, N,N-di(hydroxyalkyl)ammonium, and N-(hydroxyalkyl) N-(alkyl)ammonium wherein the two alkyl groups may form, together with the nitrogen atom to which they are bonded, at least one cyclic group optionally interrupted by at least one atom chosen from nitrogen, oxygen and sulphur;

$R_1$ to $R_6$, Z, and Z', which may be identical or different, are each chosen from hydrogen, halogen, —NHSO₃H; hydroxyl; alkyl; alkoxy; alkylthio; monoalkylamino, and dialkylamino, wherein the two alkyl groups of the dialkylamino may form together with the nitrogen atom to which they are bonded, at least one cyclic group optionally interrupted by at least one atom chosen from nitrogen, oxygen and sulphur; heterocycles and nitro; aryl; acyl; alkoxycarbonyl; carboxamido; cyano; —CO₂H; —SO₃H; —PO₃H₂; and —PO₄H₂;

A', which may be identical or different, is chosen from hydrogen; hydroxyl; amino; (hydroxyalkyl)amino; monoalkylamino; (dihydroxyalkyl)amino, (hydroxyalkyl)(alkyl)amino, (dialkyl)amino, wherein the two alkyl groups of the (dialkyl)amino may form, together with the nitrogen atom to which they are bonded, at least one cyclic group optionally interrupted by at least one atom chosen from nitrogen, oxygen and sulphur; and R is chosen from hydrogen, halogens, hydroxyl, alkoxy, and alkylthio and (B) observing a pause time; and (C) rinsing the keratin fibers.

27. The method according to claim 26, wherein the keratin fibers are human keratin fibers.

28. The method according to claim 27, wherein the human keratin fibers are hair.

29. The method according to claim 26, wherein the pause time observed ranges from about 3 minutes to about 50 minutes.

30. The method according to claim 29, wherein the pause time observed ranges from about 5 minutes to about 30 minutes.

31. A method for dyeing keratin fibers comprising (A) applying at least one dye composition comprising, in a cosmetic medium suitable for dyeing,
at least one oxidation base and optionally at least one coupler, and
at least one dye chosen from either formulae (II) and (IIbis) and the tautomeric forms thereof and the addition salts thereof or from formulae (I) and (Ibis), and the tautomeric forms thereof and the addition salts thereof:

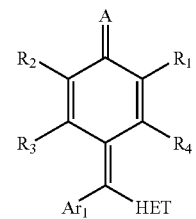
(I)

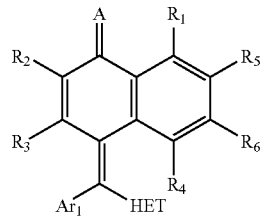
(Ibis)

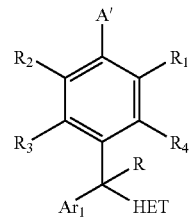
(II)

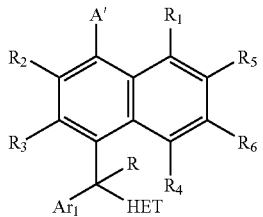
(IIbis)

wherein:

Ar₁, which may be identical or different, is chosen from aryl optionally substituted with at least one Z group;

HET, which may be identical or different, is chosen from heterocycles optionally substituted with at least one Z' group;

A, which may be identical or different, is chosen from O; NH; N-alkyl; N-hydroxyalkyl; ammonium, N-alkylammonium, N-(hydroxyalkyl)ammonium, N,N-dialkylammonium, N,N-di(hydroxyalkyl)ammonium, and N-(hydroxyalkyl) N-(alkyl)ammonium wherein the two alkyl groups may form, together with the nitrogen atom to which they are bonded, at least on cyclic group optionally interrupted by at least one atom chosen from nitrogen, oxygen and sulphur;

$R_1$ to $R_6$, Z, and Z', which may be identical or different, are each chosen from hydrogen, halogen, —$NHSO_3H$; hydroxyl; alkyl; alkoxy; alkylthio; monoalkylamino, and dialkylamino, wherein the two alkyl groups of the dialkylamino may form together with the nitrogen atom to which they are bonded, at least one cyclic group optionally interrupted by at least one atom chosen from nitrogen, oxygen and sulphur; heterocycles and nitro; aryl; acyl; alkoxycarbonyl; carboxamido; cyano; —$CO_2H$; —$SO_3H$; —$PO_3H_2$; and —$PO_4H_2$;

A', which may be identical or different, is chosen from hydrogen; hydroxyl; amino; (hydroxyalkyl)amino; monoalkylamino; (dihydroxyalkyl)amino, (hydroxyalkyl)(alkyl)amino, (dialkyl)amino, wherein the two alkyl groups of the (dialkyl)amino may form, together with the nitrogen atom to which they are bonded, at least one cyclic group optionally interrupted by at least one atom chosen from nitrogen, oxygen and sulphur; and R is chosen from hydrogen, halogens, hydroxyl, alkoxy, and alkylthio and (B) developing the color at an acid, neutral or alkaline pH by applying to the keratin fibers at least one oxidizing agent.

32. The method according to claim 31, wherein the keratin fibers are human keratin fibers.

33. The method according to claim 32, wherein the human keratin fibers are hair.

34. The method according to claim 31, wherein the at least one oxidizing agent is chosen from hydrogen peroxide, urea peroxide, alkaline metal bromates, persalts, peracids and oxidase enzymes, oxydo-reduction agents with two electrons, and oxygenases with four electrons.

35. The method according to claim 34, wherein the persalts are chosen from perborates and persulfates.

36. The method according to claim 34, wherein the oxidase enzymes are chosen from peroxidases.

37. The method according to claim 34, wherein the oxydo-reduction agents with two electrons are chosen from uricases.

38. The method according to claim 34, wherein the oxygenases with four electrons are chosen from laccases.

39. A multicompartment device or kit comprising at least two compartments wherein:
at least one compartment comprises:
at least one oxidation base and optionally at least one coupler, and
at least one dye composition comprising, in a cosmetic medium suitable for dyeing, at least one dye chosen from either formulae (II) and (IIbis) and the tautomeric forms thereof and the addition salts thereof or from formulae (I) and (Ibis), and the tautomeric forms thereof and the addition salts thereof:

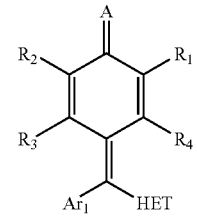
(I)

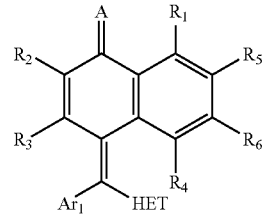
(Ibis)

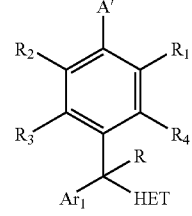
(II)

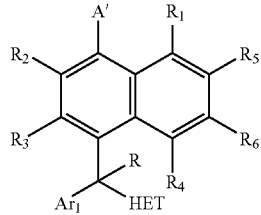
(IIbis)

wherein:
$Ar_1$, which may be identical or different, is chosen from aryl optionally substituted with at least one Z group;

HET, which may be identical or different, is chosen from heterocycles optionally substituted with at least one Z' group;

A, which may be identical or different, is chosen from O; NH; N-alkyl; N-hydroxyalkyl; ammonium, N-alkylammonium, N-(hydroxyalkyl)ammonium, N,N-dialkylammonium, N,N-di(hydroxyalkyl)ammonium, and N-(hydroxyalkyl) N-(alkyl)ammonium wherein the two alkyl groups may form, together with the nitrogen atom to which they are bonded, at least one cyclic group optionally interrupted by at least one atom chosen from nitrogen, oxygen and sulphur;

$R_1$ to $R_6$, Z, and Z', which may be identical or different, are each chosen from hydrogen, halogen, —$NHSO_3H$; hydroxyl; alkyl; alkoxy; alkylthio; monoalkylamino, and dialkylamino, wherein the two alkyl groups of the dialkylamino may form together with the nitrogen atom to which they are bonded, at least one cyclic group optionally interrupted by at least one atom chosen from nitrogen, oxygen and sulphur; heterocycles and nitro; aryl; acyl; alkoxycarbonyl; carboxamido; cyano; —$CO_2H$; —$SO_3H$; —$PO_3H_2$; and —$PO_4H_2$;

A', which may be identical or different, is chosen from hydrogen; hydroxyl; amino; (hydroxyalkyl)amino; monoalkylamino; (dihydroxyalkyl)amino, (hydroxyalkyl)(alkyl)amino, (dialkyl)amino, wherein the two alkyl groups of the (dialkyl)amino may form, together with the nitrogen atom to which they are bonded, at least one cyclic group optionally interrupted by at least one atom chosen from nitrogen, oxygen and sulphur; and R is chosen from hydrogen, halogens, hydroxyl, alkoxy, and alkylthio and at least one other compartment comprising at least one oxidizing composition.

* * * * *